US011529056B2

(12) United States Patent
Pesach et al.

(10) Patent No.: US 11,529,056 B2
(45) Date of Patent: Dec. 20, 2022

(54) CROSSTALK REDUCTION FOR INTRA-ORAL SCANNING USING PATTERNED LIGHT

(71) Applicant: Dentlytec G.P.L. LTD., Tel-Aviv (IL)

(72) Inventors: Benny Pesach, Rosh Haayin (IL); Amitai Reuvenny, Kfar-Saba (IL); Georgy Melamed, Ramat Gan (IL)

(73) Assignee: Dentlytec G.P.L. Ltd., Tel Aviv (IL)

( * ) Notice: Subject to any disclaimer, the term of this patent is extended or adjusted under 35 U.S.C. 154(b) by 293 days.

(21) Appl. No.: 16/343,337

(22) PCT Filed: Oct. 18, 2017

(86) PCT No.: PCT/IL2017/051150
§ 371 (c)(1),
(2) Date: Apr. 18, 2019

(87) PCT Pub. No.: WO2018/073824
PCT Pub. Date: Apr. 26, 2018

(65) Prior Publication Data
US 2019/0254529 A1  Aug. 22, 2019

Related U.S. Application Data

(60) Provisional application No. 62/409,670, filed on Oct. 18, 2016.

(51) Int. Cl.
*A61B 5/00* (2006.01)
*G01B 11/25* (2006.01)
*G06T 7/521* (2017.01)

(52) U.S. Cl.
CPC .......... *A61B 5/0088* (2013.01); *A61B 5/0062* (2013.01); *A61B 5/0064* (2013.01);
(Continued)

(58) Field of Classification Search
None
See application file for complete search history.

(56) References Cited

U.S. PATENT DOCUMENTS 6,252,623 B1   6/2001  Lu et al.
6,549,288 B1   4/2003  Migdal et al.
(Continued)

FOREIGN PATENT DOCUMENTS

EP          2026034        2/2009
WO     WO 2016/188939 A1  12/2016
(Continued)

OTHER PUBLICATIONS

Feng et al. "Monte Carlo Simulations of Photon Migration Path Distributions in Multiple Scattering Media", Proceeding of the SPIE, 1888, Photon Migration and Imaging in Random Media and Tissues, 1888: 77-89, Sep. 14, 1993.
Fried et al. "Nature of Light Scattering in Dental Enamel and Dentin at Visible and Near-Infrared Wavelengths", Applied Optics, 34(7): 1278-1285, Mar. 1, 1995.
(Continued)

*Primary Examiner* — Tahmina N Ansari
(74) *Attorney, Agent, or Firm* — Cooley LLP

(57) ABSTRACT

According to some embodiments there is provided a method for structured light scanning of an intra-oral scene, comprising: projecting onto the intra-oral scene a color-coded pattern comprising an arrangement of entities having edges between them; each entity comprising a different narrow band of wavelengths; and detecting the projected pattern as a plurality of pixels in an acquired image of the scene using at least two narrowband filters, wherein for each pixel of at least 95% of the pixels of an entity of interest comprising a first band of wavelengths, a contribution of light from a second band of wavelengths of an adjacent entity is less than 10%.
Some embodiments relate to a scanner system for structured light scanning of an intra-oral scene.

22 Claims, 19 Drawing Sheets

(52) U.S. Cl.
CPC ........ *A61B 5/0075* (2013.01); *G01B 11/2509* (2013.01); *A61B 5/4547* (2013.01); *G06T 7/521* (2017.01); *G06T 2207/10024* (2013.01)

(56) References Cited

U.S. PATENT DOCUMENTS

| | | | |
|---|---|---|---|
| 7,494,338 B2* | 2/2009 | Durbin ............... | A61C 9/00 433/29 |
| 7,724,932 B2 | 5/2010 | Ernst et al. | |
| 9,325,966 B2 | 4/2016 | Tin | |
| 9,454,846 B2 | 9/2016 | Pesach et al. | |
| 9,593,982 B2 | 3/2017 | Rhoads et al. | |
| 10,159,542 B2* | 12/2018 | Pesach ............... | A61C 1/0069 |
| 10,966,614 B2* | 4/2021 | Pesach ............... | G01B 11/25 |
| 2005/0089214 A1 | 4/2005 | Rubbert et al. | |
| 2006/0154198 A1* | 7/2006 | Durbin ............ | A61C 9/0053 433/29 |
| 2006/0279820 A1 | 12/2006 | Riley et al. | |
| 2008/0063998 A1* | 3/2008 | Liang ............... | A61B 5/4547 433/29 |
| 2009/0221874 A1 | 9/2009 | Vinther et al. | |
| 2010/0284589 A1 | 11/2010 | Thiel et al. | |
| 2010/0311005 A1* | 12/2010 | Liang ............... | A61B 5/1079 433/29 |
| 2011/0074932 A1 | 3/2011 | Gharib et al. | |
| 2018/0067327 A1 | 3/2018 | Peng et al. | |
| 2018/0106593 A1 | 4/2018 | Arden et al. | |
| 2018/0125338 A1* | 5/2018 | Pfeiffer ............. | G01B 11/25 |
| 2018/0299262 A1 | 10/2018 | Thiel et al. | |
| 2019/0254529 A1* | 8/2019 | Pesach ............. | A61B 5/0088 |
| 2019/0259205 A1 | 8/2019 | Nissinen et al. | |
| 2021/0162657 A1 | 6/2021 | Chartrain et al. | |

FOREIGN PATENT DOCUMENTS

| | | |
|---|---|---|
| WO | WO 2018/073824 A1 | 4/2018 |
| WO | WO 2019/207588 A2 | 10/2019 |

OTHER PUBLICATIONS

International Preliminary Report on Patentability dated May 2, 2019 From the International Bureau of WIPO Re. Application No. PCT/IL2017/051150. (9 Pages).

International Search Report and the Written Opinion dated Jan. 25, 2018 From the International Searching Authority Re. Application No. PCT/IL2017/051150. (22 Pages).

Lapray et al. "Multispectral Filter Arrays: Recent Advances and Practical Implementation", Sensors, 14(11): 21626-21659, Nov. 17, 2014.

Zhang et al. "Rapid Shape Acquisition Using Color Structured Light and Multi-Pass Dynamic Programming", 2002 Proceedings of the First International Symposium on 3D Data Processing and Visualization and Transmission, Padua, Italy, Jun. 19-21, 2002, 13 P., Jun. 19, 2002.

Invitation to Pay Additional Fees, Communication Relating to the Results of the Partial International Search and the Provisional Opinion dated Aug. 7, 2019 From the International Searching Authority Re. Application No. PCT/IL2019/050464. (13 Pages).

Supplementary European Search Report and the European Search Opinion dated May 15, 2020 From the European Patent Office Re. Application No. 17862210.6. (9 Pages).

Communication Pursuant to Article 94(3) EPC dated Nov. 10, 2021 From the European Patent Office Re. Application No. 17862210.6. (5 Pages).

Notice of Allowance dated Mar. 16, 2022 from US Patent and Trademark Office Re. U.S. Appl. No. 17/050,365. (8 pages).

Official Action dated Aug. 30, 2021 from the US Patent and Trademark Office Re. U.S. Appl. No. 17/050,365. (15 pages).

International Preliminary Report on Patentability dated Nov. 5, 2020 From the International Bureau of WIPO Re. Application No. PCT/IL2019/050464. (12 Pages).

International Search Report and the Written Opinion dated Nov. 11, 2019 From the International Searching Authority Re. Application No. PCT/IL2019/050464. (20 Pages).

\* cited by examiner

13A
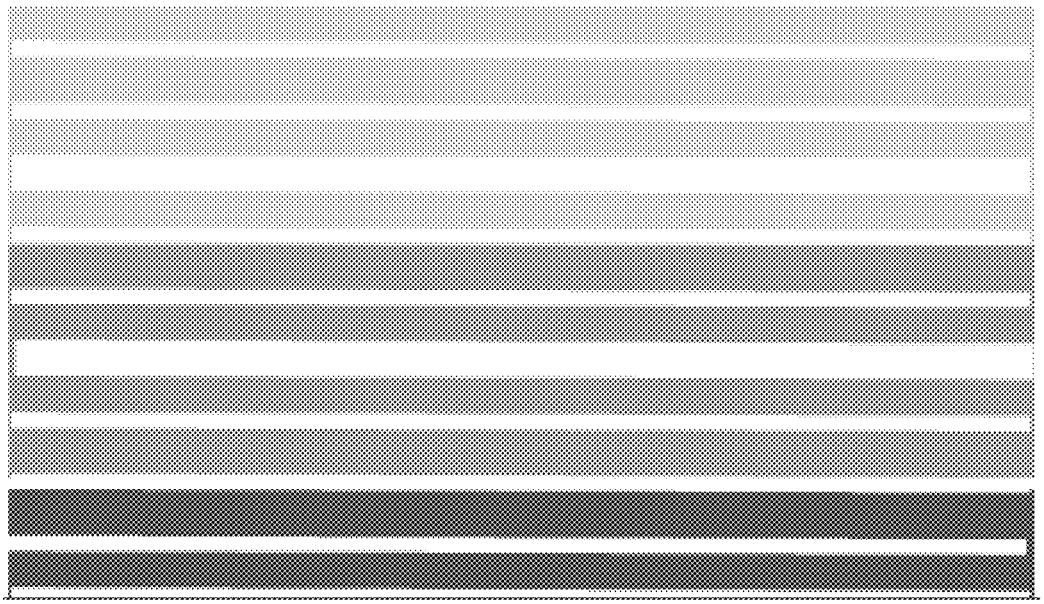
13B
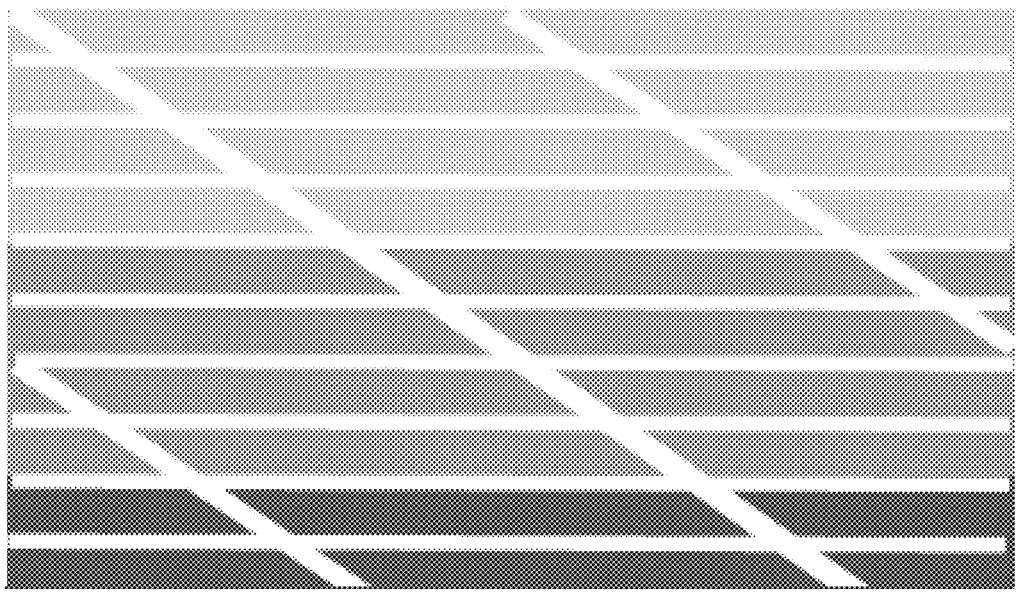
FIGs. 13A-B

FIG. 18A

| B1 | C  | C  | C  | C  | B1 | C  |
|----|----|----|----|----|----|----|
| C  | B2 | C  | C  | C  | C  | B2 |
| C  | C  | B3 | C  | C  | C  | C  |
| C  | C  | C  | B4 | C  | C  | C  |
| C  | C  | C  | C  | B5 | C  | C  |
| B1 | C  | C  | C  | C  | B1 | C  |
| C  | B2 | C  | C  | C  | C  | B2 |

FIG. 18B

| B1 | C | B3 | C | B5 | C | B2 |
|----|---|----|---|----|---|----|
| B2 | C | B4 | C | B1 | C | B3 |
| B1 | C | B3 | C | B5 | C | B2 |
| B2 | C | B4 | C | B1 | C | B3 |
| B1 | C | B3 | C | B5 | C | B2 |
| B2 | C | B4 | C | B1 | C | B3 |
| B1 | C | B3 | C | B5 | C | B2 |

CROSSTALK REDUCTION FOR INTRA-ORAL SCANNING USING PATTERNED LIGHT

RELATED APPLICATIONS

This application is a National Phase of PCT Patent Application No. PCT/IL2017/051150 having International filing date of Oct. 18, 2017, which claims the benefit of priority under 35 USC § 119(e) of U.S. Provisional Patent Application No. 62/409,670 filed on Oct. 18, 2016. The contents of the above applications are all incorporated herein by reference as if fully set forth in their entirety.

FIELD AND BACKGROUND OF THE INVENTION

The present invention, in some embodiments thereof, relates to dental measurements, and more particularly, but not exclusively, to optical patterns for intra-oral scanning.

U.S. Pat. No. 7,724,932 B2 to Maurice et al. discloses "A method for creating three-dimensional models of intra-oral scenes and features. The intra-oral scene is illuminated by a two-dimensional array of structured illumination points, with anti-aliasing achieved by using stored two-dimensional patterns of pixels for anti-aliasing. Using a single camera to form images reduces the amount of apparatus necessary to introduce into the patient's mouth. Three-dimensional models are obtained from the single image by triangulation with a stored image of the structured illumination onto a reference surface such as a plane. Alternative methods include the use of "bar-coded" one-dimensional patterns." (Abstract)

Rapid shape acquisition using color structured light and multi-pass dynamic programming" L Zhang, B Carless, S M Seitz—3D Data Processing, 2002, appears to present, "a color structured light technique for recovering object shape from one or more images. The technique works by projecting a pattern of stripes of alternating colors and matching the projected color transitions with observed edges in the image. The correspondence problem is solved using a novel, multi-pass dynamic programming algorithm that eliminates global smoothness assumptions and strict ordering constraints present in previous formulations. The resulting approach is suitable for generating both high-speed scans of moving objects when projecting a single stripe pattern and high-resolution scans of static scenes using a short sequence of time-shifted stripe patterns. In the latter case, space-time analysis is used at each sensor pixel to obtain inter-frame depth localization. Results are demonstrated for a variety of complex scenes."

U.S. Pat. No. 9,593,982 apparently discloses, "A smartphone," "adapted for use as an imaging spectrometer, by synchronized pulsing of different LED light sources as different image frames are captured by the phone's CMOS image sensor. A particular implementation employs the CIE color matching functions, and/or their orthogonally transformed functions, to enable direct chromaticity capture. A great variety of other features and arrangements are also detailed."

All of which are incorporated herein by reference

SUMMARY OF THE INVENTION

According to an aspect of some embodiments of the invention, there is provided a method for structured light scanning of an intra-oral scene, comprising projecting onto the intra-oral scene a color-coded pattern comprising an arrangement of entities having edges between them; each entity comprising a different narrow band of wavelengths; and detecting the projected pattern as a plurality of pixels in an acquired image of the scene using at least two narrow-band filters, wherein for each pixel of at least 95% of the pixels of an entity of interest comprising a first band of wavelengths, a contribution of light from a second band of wavelengths of an adjacent entity is less than 10%.

According to an aspect of some embodiments of the invention, there is provided a method for structured light scanning of an intra-oral scene, including projecting onto the intra-oral scene a color-coded pattern including an arrangement of entities having edges between them; each entity including a different wavelength bands; detecting the projected pattern as a plurality of pixels in an acquired image of the scene, and differentiating between the different wavelength bands in the image by separating between at least two spectral bands wherein at least one of the spectral bands a narrow band; restoring the projected pattern by associating an imaged entity to a projected entity by identifying the wavelength band of the projected entity in the image.

According to some embodiments of the invention, the differentiated is performed using at least two narrowband filters.

According to some embodiments of the invention, at least one of the at least two narrowband filters captures least 95% of the pixels of the at least one spectral band.

According to some embodiments of the invention, the differentiating is into at least 5 wavelength bands.

According to some embodiments of the invention, at least one of the filters includes an interference filter.

According to some embodiments of the invention, the pattern entities includes parallel stripes.

According to some embodiments of the invention, the pattern includes at least 8 different wavelength bands.

According to some embodiments of the invention, the at least wavelength bands are selected from the range of 400-500 nm.

According to some embodiments of the invention, the differentiating is effective to reduce spatial crosstalk between the pattern entities, caused as a result of volume scattering of the projected light inside contents of the intra-oral scene.

According to some embodiments of the invention, the different wavelengths are projected and/or detected simultaneously.

According to some embodiments of the invention, the different wavelengths are projected and/or detected sequentially in time.

According to an aspect of some embodiments of the invention, there is provided a scanner system for imaging an intra-oral scene including: an intraoral portion sized and shaped for insertion into the oral cavity, the intraoral portion including: a light source configured for projecting a color-coded pattern onto the intra-oral scene; a spectral imager positioned to image the scene.

According to some embodiments of the invention, the pattern includes lines in at least one direction.

According to some embodiments of the invention, the imager includes an array of pixels arranged in lines at an angle between 45 to 90 degrees of the direction of the at least one direction.

According to some embodiments of the invention, the imager includes at least one wide band sensor.

According to some embodiments of the invention, a bandwidth of the wide band sensor is at least 50% the combined bandwidth of all of the spectral sensors in the imager.

According to some embodiments of the invention, the spectral imager includes at least two narrowband filters suitable for detecting at least two different wavelength bands of the pattern.

According to some embodiments of the invention, at least one of the filters includes an interference filter.

According to some embodiments of the invention, the different wavelength bands are detected by different pixels of the imager.

According to some embodiments of the invention, pixels of the imager are covered with interference filters that match the different wavelength bands of the pattern.

According to some embodiments of the invention, at least one of the filters is tunable and is configured for detecting the different wavelength bands sequentially.

According to some embodiments of the invention, the light source includes a plurality of LEDs arrayed adjacent each other, each LED configured for emitting light at one of the different wavelength bands.

According to some embodiments of the invention, the light source is a wide spectrum light source, and wherein a set of filters suitable for transmitting the selected wavelengths are illuminated by the light source for projecting the color-coded pattern onto the scene.

According to some embodiments of the invention, the light source is a wide spectrum light source, and wherein a grating that diffracts light from the wide spectrum light source forms at least one of the components for projecting the color-coded pattern onto the scene.

According to some embodiments of the invention, the light source is a variable wavelength source.

According to some embodiments of the invention, the imager is a hyperspectral imager.

According to some embodiments of the invention, the imager is a hyperspectral imager including at least 5 spectral bands.

According to an aspect of some embodiments of the invention, there is provided a method for structured light scanning of an intra-oral scene, including projecting onto the intra-oral scene a color-coded pattern including color entities separated from each other by dark regions; acquiring and image of the intra-oral scene; and detecting the projected pattern in the acquired image of the scene; and determining one or more depths in the scene.

According to some embodiments of the invention, the dark regions are sized to reduce optical crosstalk by being large enough so as to avoid geometrical overlap between the imaged entities.

According to some embodiments of the invention, the acquiring is performed using a color imager including a Bayer filter.

According to some embodiments of the invention, the color imager is an RGB (Red Blue Green) color imager.

According to some embodiments of the invention, the color imager is an RGBI (Red Blue Green IR) color imager.

According to some embodiments of the invention, the detecting includes determining colors in the imaged pattern using the dark regions as reference.

According to some embodiments of the invention, the pattern entities comprise parallel stripes.

According to some embodiments of the invention, the pattern includes colored stripes separated from each other by dark regions in the form of stripes.

According to some embodiments of the invention, the determining includes subtracting the color obtained in a dark region from the color obtained in a stripe of interest to reduce spectral crosstalk.

According to some embodiments of the invention, the dark region includes a non-illuminated area.

According to some embodiments of the invention, the detecting includes indexing the color entities of the pattern, and wherein the dark regions define entities of the pattern which can be indexed in addition to the color entities.

According to an aspect of some embodiments of the invention, there is provided a method for structured light scanning of an intra-oral scene, including acquiring at least one image of the intra-oral scene under unstructured lighting; acquiring at least one image of the intra-oral scene under patterned lighting; and constructing a 3D model of the scene using inner-image information obtained from the image acquired under unstructured lighting and inner-image information obtained from the image acquired under the patterned lighting.

According to some embodiments of the invention, the unstructured lighting includes uniform lighting.

According to some embodiments of the invention, the method includes sequentially interchanging between the acquiring of a uniform light image and the acquiring of a patterned image.

According to some embodiments of the invention, the constructing includes identifying borders of smooth patches in the scene, the borders indicative of depth discontinuities, and wherein the smooth patches are indexed in a continuous manner.

According to some embodiments of the invention, information obtained from the image acquired under unstructured lighting is used for one or more of: coloring of the reconstructed scene, assessment of a geometry of the scene, evaluation of reflection characteristics of contents of the scene, and assessment of locations prone to loss of a projected pattern entities.

According to some embodiments of the invention, the patterned lighting includes projecting, onto the intra-oral scene, a pattern including a recurrent arrangement of parallel stripes.

According to some embodiments of the invention, the pattern includes one or more anchors.

According to some embodiments of the invention, the anchors are in the form of diagonals intersecting the stripes.

According to some embodiments of the invention, the stripes are of various widths.

According to some embodiments of the invention, the pattern includes multiple color zones.

According to an aspect of some embodiments of the invention, there is provided a method for structured light scanning of an intra-oral scene, including projecting onto the intra-oral scene a pattern including a recurring arrangement of stripes, the pattern including one or more anchors in the form of diagonals intersecting the stripes; and detecting the projected pattern in an acquired image of the scene.

According to some embodiments of the invention, the method further includes constructing a 3D model of the scene, the constructing including restoring the pattern in the acquired image utilizing the one or more anchors.

According to some embodiments of the invention, the method further includes indexing the anchors directly and further indexing the stripes or portions thereof in accordance with their spatial location relative to the anchors.

According to some embodiments of the invention, an amount of anchors incorporated in the pattern is selected in accordance with a scene variability.

According to an aspect of some embodiments of the invention, there is provided a method for depth imaging using structured light, including projecting onto a scene a color-coded pattern including an arrangement of entities; each entity including a different band of wavelengths; imaging the projected pattern as a plurality of pixels in an acquired image of the scene, using at least first and second spectral filters; wherein at least a first portion of the plurality of pixels is associated with the first filter and at least a second portion of the plurality of pixels is associated with the second filter; and wherein in the first portion of the plurality of pixels there is less than 10% contribution of the wavelength band transferred by the second filter; estimating the color of each pixel for associating the pixel with the projected color-coded pattern; and determining depth in the scene according to the associating.

According to some embodiments of the invention, the color coded pattern includes at least 5 wavelength bands and wherein each of the pixels of the acquired image is associated with one of 5 matching filters.

According to some embodiments of the invention, the pixels associated with filters are evenly distributed over an image sensor of an imager configured for acquiring the image.

According to some embodiments of the invention, the filters associated with the pixels are interference filters attached to the pixels.

According to an aspect of some embodiments of the invention, there is provided a method for structured light scanning of an intra-oral scene, including projecting onto the intra-oral scene a color-coded pattern including an arrangement of entities having edges between them; each entity including a different wavelength bands; detecting the projected pattern as a plurality of pixels in an acquired image of the scene, and differentiating between the different wavelength bands in the image by separating between at least two spectral bands; restoring the projected pattern by associating an imaged entity to a projected entity by identifying the wavelength band of the projected entity in the image wherein the at least wavelength bands are selected from the range of 400-500 nm.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

Implementation of the method and/or system of embodiments of the invention can involve performing or completing selected tasks manually, automatically, or a combination thereof. Moreover, according to actual instrumentation and equipment of embodiments of the method and/or system of the invention, several selected tasks could be implemented by hardware, by software or by firmware or by a combination thereof using an operating system.

For example, hardware for performing selected tasks according to embodiments of the invention could be implemented as a chip or a circuit. As software, selected tasks according to embodiments of the invention could be implemented as a plurality of software instructions being executed by a computer using any suitable operating system. In an exemplary embodiment of the invention, one or more tasks according to exemplary embodiments of method and/or system as described herein are performed by a data processor, such as a computing platform for executing a plurality of instructions. Optionally, the data processor includes a volatile memory for storing instructions and/or data and/or a non-volatile storage, for example, a magnetic hard-disk and/or removable media, for storing instructions and/or data. Optionally, a network connection is provided as well. A display and/or a user input device such as a keyboard or mouse are optionally provided as well.

BRIEF DESCRIPTION OF THE SEVERAL VIEWS OF THE DRAWINGS

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings:

FIGS. 13A-B are examples of patterns comprising color zones, according to some embodiments of the invention;

FIGS. 18A and 18B illustrate structures of a sensor array in accordance with embodiments of the current invention.

DESCRIPTION OF SPECIFIC EMBODIMENTS OF THE INVENTION

Figure 1:
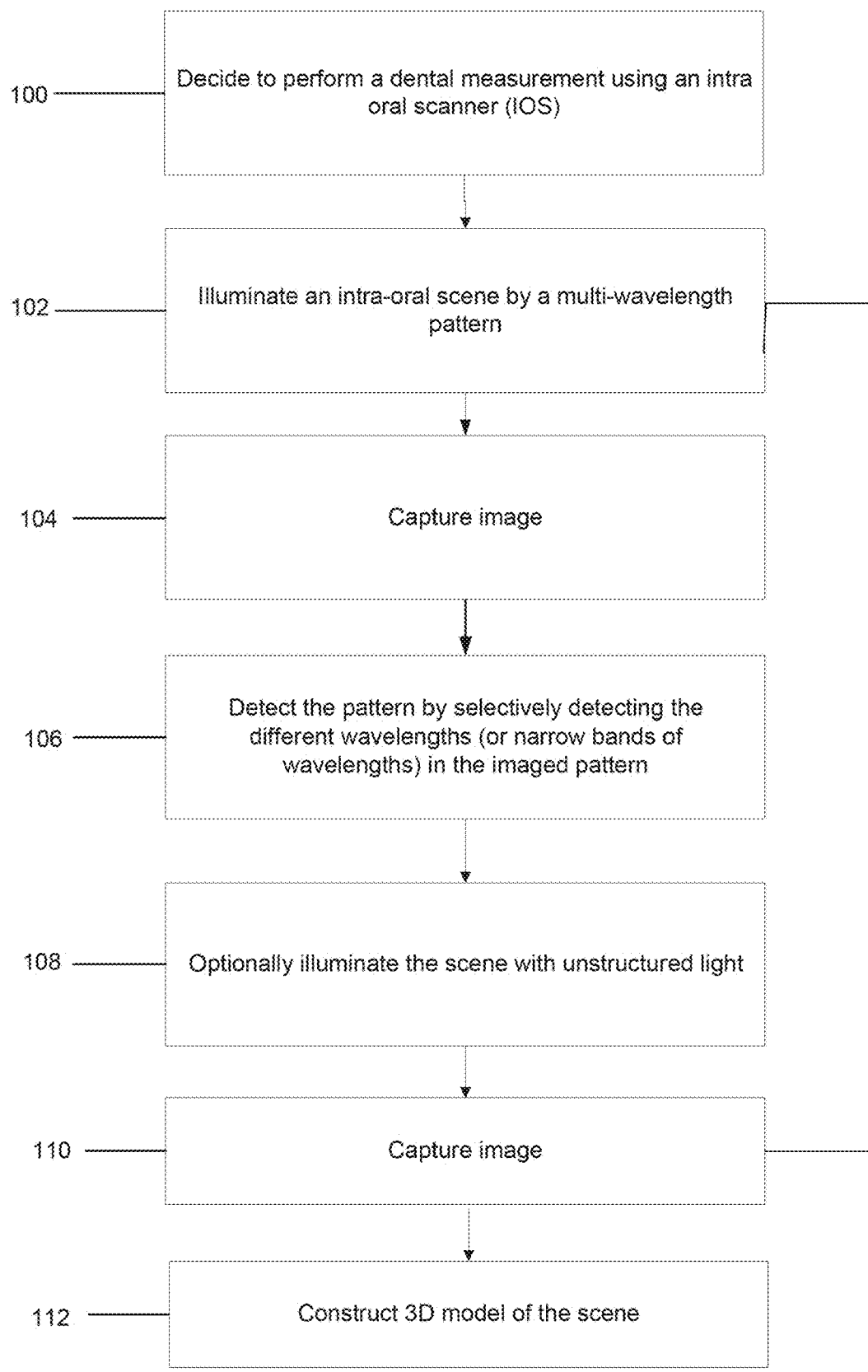
FIG. 1 is a flowchart of a method for scanning an intra-oral scene by projecting a multi-wavelength pattern and separating the different wavelengths upon detection of the pattern, according to some embodiments of the invention.

The present invention, in some embodiments thereof, relates to dental measurements, and more particularly, but not exclusively, to optical patterns for intra-oral scanning.

Some embodiments of the invention relate to use of structured light for constructing a 3D model of the intra-oral scene. In some embodiments, scanning is performed using a hand-held intra oral scanner (IOS) configured for projecting one or more patterns onto the intra-oral scene, and imaging the scene with at least one imager.

A broad aspect of some embodiments of the current invention relates to reducing cross talk between structured illumination entities in dental imaging. For example spatial crosstalk and/or misidentification of projected entities may result in inaccurate measurements of structure. Optionally, spectral differentiation is used to identify projected entities and/or reduce spatial crosstalk.

In some embodiments, narrow band illumination and/or spectral imaging are used to reduce spectral crosstalk. Optionally, reducing spectral crosstalk reduces misidentification of a projected object. In some cases, misidentification of a projected object may lead to an incorrect model of the structure, geometry of an object. For example, an imager with narrow band filters may be used to reduce spectral crosstalk.

In some embodiments, crosstalk is caused by properties of the measurement device and/or the light projector and/or due to ambient light and/or due to properties of the object being imaged. In some embodiments, use of spectral differentiation may reduce one some or all of these forms of crosstalk.

An aspect of some embodiment of the current invention relates to projecting spectrally differentiated entities separated by dark areas onto a dental scene. Optionally, a dark area is imaged. For example, measurements of light imaged in a dark area may be used to correct an effect of ambient light and/or to correct an effect of smearing on a measured light a projected entity.

An aspect of some embodiments of the present invention relates to choosing spectral bands that can produce accurate images on a dental surface. For example, high frequency light may be used to reduce scattering caused by translucency of teeth. For example, multiple narrow bands of light may be projected in the blue-violet bands. Narrow spectral filters are optionally used to differentiate between the narrow illumination bands.

An aspect of some embodiments of present invention relates to using both monochrome and spectrally differentiated projected objects and/or detection bands. Optionally, monochrome imaging is used to increase sensitivity. Optionally, spectral differentiation is used to recognize a projected object and/or to reduce crosstalk.

An aspect of some embodiments of the current invention relates to adapting a spectral imager to imaging of a dental scene. For example, a Bayer filter imager may be configured with additional pixel sensors in high frequency (violet-blue-green bands) and/or fewer sensors in the low frequency (red) bands. Alternatively or additionally, the sensor may include a mixture of black and white pixel sensors and color sensors.

A broad aspect of some embodiments of the invention relates to spatial coding using a light pattern. In some embodiments, due to the plurality of tissue types, structures and/or materials (natural and/or artificially introduced materials) in the intra-oral scene, and/or due to properties of the optical elements of the IOS, the imaged pattern is smeared relative to the one that was projected. Some embodiments of the invention relate to identifying and separating the projected pattern entities from each other in an image. For example, the image may be used for reconstructing the pattern in a model of the scene.

In some embodiments, when choosing a light pattern that can be successfully restored, one or more restrictions such as the plurality of imaged materials, optical properties of the teeth and tissues, and/or inherent intra and/or extra-oral movement of the operator (which may limit time sequencing of the pattern with respect to the IOS's FPS rate) are taken into consideration.

An aspect of some embodiments relates to projection of a pattern onto an intra-oral scene and/or detection of the pattern that are suitable to reduce optical crosstalk between adjacent pattern entities, such as stripes. In some embodiments, crosstalk between the pattern entities is reduced by utilizing black spaces between adjacent pattern entities. Alternatively or additionally, optical crosstalk may be reduced by using spectrally differentiated projected entities and spectral differentiation, for example using an imaging spectrometer (e.g. a color camera and/or a hyperspectral camera). Optionally, the use of spectral differentiation reduces crosstalk between nearby projected entities. For example, increasing the specificity of the spectral differentiation may facilitate differentiation of projected entities with smaller black spaces and/or without the use of black spaces. For example, spectral differentiation may by increased by narrowing the width of a detected spectral band. For example in some embodiments, a hyperspectral camera may increase spectral differentiation and/or reduce spectral crosstalk compared to a Bayer filter camera.

In some embodiments, crosstalk may be reduced by wavelength coding. For example, wavelength coding may be advantageous in the case of significant smearing (e.g. as in projecting pattern over a tooth). For example, wavelength coding may be advantageous, when imaging teeth. In some embodiments, wavelength coding includes projecting a series of colored lines. For example, the colored lines be projected in a de Bruijn colored sequence. In some embodiments, light pattern projection methods and/or image acquiring methods may include techniques and/or equipment as described, for example, in "Rapid shape acquisition using color structured light and multi-pass dynamic programming" L Zhang, B Curless, S M Seitz—3D Data Processing, 2002.

In some cases, optical crosstalk includes spatial crosstalk. For example, spatial crosstalk may include smearing of a light pattern over space. In some cases, spatial crosstalk may be caused as by of scattering of the projected light. For example, scattering can be caused by a tooth and/or other oral contents. For example, some light striking a translucent object may be reflected at the surface and some of the light may enter the material and be reflected from a location under this surface. The reflected light may appear as a smeared signal of mixed light from different locations. This first type of crosstalk, which can be referred to as "spatial crosstalk", may vary spatially, and be affected, for example, by one or more of: the scattering coefficients of the tissue and/or other oral content, the scanner optics modulation transfer function limitations, unwanted movement of the scanner and/or other factors.

In some cases optical crosstalk includes spectral crosstalk. For example, spectral crosstalk may be affected by one or more of: the light source spectrum, pattern transparency and/or the imager's spectral filters, and/or other factors. In some embodiments, spectral crosstalk may occur when light in one waveband is detected by a sensor measuring a different waveband. For example, spectral crosstalk caused only by known limitation of a device may be constant. In some embodiments known, constant crosstalk is taken into consideration before and/or during processing of the imaged pattern.

In some embodiments, spatial crosstalk is reduced or eliminated by applying algorithms designed to remove the crosstalk. In some embodiments, the spectral crosstalk, which, in some cases, is of known and constant properties, is reduced or eliminated by applying image pre-processing with pre-calibrated coefficients and/or by using one an spectral imager at detection. For example, a spectral imager may include a filtered camera (for example a conventional color imager including for pixel filters) and/or a hyperspectral imager. For example, a hyperspectral imager may include a whiskbroom scanner, a pushbroom scanner, an integral field spectrograph (and/or a device employing related dimensional reformatting techniques), a wedge imaging spectrometer, a Fourier transform imaging spectrometer, a computed tomography imaging spectrometer (CTIS), an image replicating imaging spectrometer (IRIS), a coded aperture snapshot spectral imager (CASSI), and/or image mapping spectrometer (IMS).

In some embodiments in which spatial crosstalk is significant, such as in the case of imaging teeth using structured light, the spatial crosstalk causes smearing of the structured light pattern. For example, spatial crosstalk may make it difficult to reconstruct the pattern and/or make it difficult to associate the image of the pattern with the projected pattern. In some embodiments, the reconstructed pattern is used to produce a depth map. In some cases, a pattern having higher density of entities is used to reach a higher resolution and/or higher accuracy of the measured depth. Smearing, for example, due to spatial crosstalk, may in some instance make it difficult to reconstruct the pattern, reduce the resolution of highly dense patterns. For example, spatial crosstalk may reduce the resolution and/or accuracy of measurements.

In some cases, in which smear or spatial crosstalk is significant, for example when pattern is illuminated on a translucent material such as a tooth, the projected stripes may spatially mix together. In case of spectral crosstalk, stripes of different wavelengths may excite the same detector. For example, the combination of spatial crosstalk and spatial crosstalk may cause projected stripes at different locations and/or wavelengths "mix." For example, lines projected at different locations and/or wavelengths may mix through the translucent teeth and/or be received together by the same sensor, making it difficult to reconstruct the color of the stripes and/or the location of the edge between the stripes.

In some embodiments, spectral differentiation may be used to reduce spatial crosstalk. For example, adjacent and/or nearby projected entities may have different spectral signatures. Light mixed between two entities may be removed by spectral methods. For example, spectral differentiation may produce combined spectral and/or spatial data in the form of a color image and/or multiple narrow band images and/or hyperspectral data cube. The resulting data is used, for example, to determine the position of each projected entity with reduced crosstalk from other entities.

In some embodiments, multi spectral imaging may be used. For example an image may be acquired with a conventional Bayer filter based color camera and/or an narrow band imager based on three, four, or five color differentiation (e.g. narrow band Red, Blue, Green (RGB) filters and/or an infrared (IR) filter and/or an ultraviolet (IR) filter In some embodiments, hyperspectral imaging may be used to reduce spectral crosstalk that may occur when an image is acquired with a multispectral imager. In some embodiments, hyperspectral imaging may break the spectrum into more than 4 and/or more than 5 and/or more than 8 and/or more than 20 different bands. Alternatively or additionally, hyperspectral imaging may break the spectrum into narrow bands. For example, narrow bands may have reduced overlap over Bayer Filter RGB imaging. For example, a convention magenta filter may allow unintended green light to leak into an image. Hyperspectral filters may include orthogonal colors and/or reduce spectral crosstalk. Optionally, a hyperspectral imager may include a camera with an interference filter. For example, there may be an interference filter on each pixel.

In some embodiments, a hyperspectral imager may be used to detect a signal. Optionally, a hyperspectral camera comprises one or more narrowband filters. Optionally, a color pattern comprising a plurality of narrowband colors is projected, and a hyperspectral camera comprising matching narrowband filters is used for acquiring the image. A potential advantage of separation between the color channels may include facilitating reconstruction of the color and/or location of each stripe. In some embodiments, the hyperspectral camera measures the intensity of each color channel at each hyperspectral pixel, and identifies the strongest color channel as the correct color, neglecting the contribution of color channels having lower intensities at the pixel. A potential advantage of using a hyperspectral camera may include facilitating estimating the colors of the projected color pattern, for example in cases in which the color is altered by spectral reflectance properties of the object, smear, spatial crosstalk, etc. Factors affecting the received color may include material type, color of the object, specular reflections, diffuse reflection, bulk scattering and absorption, translucency, local pigmentation, stain, ambient illumination, light incidence angle and/or other factors.

An aspect of some embodiments relates to using at least one narrowband filter for detection of a pattern projected onto an intra-oral scene. In some embodiments, an intra-oral scene is illuminated using a plurality of wavelengths (or a plurality of different narrow bands of wavelengths), and a plurality of narrowband filters are used for selectively receiving the plurality of wavelengths (or narrow bands) at detection.

In some cases non-uniform reflection of light, for example light returning from translucent tooth bulk portions (e.g. other than an external surface onto which the light was projected) results in smearing of adjacent pattern stripes. This smearing may lead to crosstalk between the differently colored stripes, making color reconstruction more difficult.

Misidentification of color may lead to errors in identifying a relative spatial location in the pattern, which may further result in errors in constructing the 3D model. In some embodiments, by using a narrowband detector, the effect of inherent smearing and/or spatial crosstalk of the projected light by the different structures and/or materials in the intra-oral scene may be mitigated. Optionally the narrowband detector is designed to capture selected wavelengths of light and/or to reduce spectral crosstalk. Optionally reducing since spectral crosstalk may increase the system's sustainability and/or reduce processing errors. For example, a potential advantage of using a narrowband illumination coding and detectors may include increasing the system's sustainability, and/or reducing processing errors, and/or reduce crosstalk (e.g. including spectral and/or spatial crosstalk).

In some embodiments, one or more interference filters are used for detecting the pattern. Additionally or alternatively, one or more dichroic filters are used for detecting the pattern. In some embodiments, liquid crystal based filters may be used.

In some embodiments, spectral crosstalk is reduced at detection such that in any pixel of a first imaged pattern entity comprising a first wavelength (or narrow band of wavelengths) there is less than 1% less than 5% less than 10%, less than 20%, less than 30% contribution of a second wavelength (or narrow band of wavelengths) of an adjacent pattern entity. Reducing crosstalk may, in some embodiments, reduce risk of misidentifying a color, for example, pattern entity's color. For example reducing crosstalk may reduce the probability of mistakenly identifying an observed color as one of the other colors in a pattern. In some embodiments, the number and/or order of colors in a pattern is selected for reducing ambiguity. For example increasing the number of different colors in a pattern and/or decreasing the distance between different colored projections may increase the precision of determining a position of an illuminated object. Alternatively or additionally, the number of colors in a pattern may be reduced and/or the distance between differently colored locations may be increased and/or the order adjusted to reduce the risk misidentification of a color and/or mistaking one color for another color that exists in the pattern. Optionally, the number of colors, the order of colors and/or the width of bands may be adjusted according to the required depth range, the required precision, the baseline distance between the pattern projector and imager, and/or the pattern density. For example, misidentification of a color may occur as a result of spectral crosstalk. Misidentification may increase as the spectral overlap between the different spectral bands increases. For example, spectral overlap may depend on the spectral range and/or the spectral width of the different pattern colors.

In some cases, spectral misidentification may increase due to spatial overlap and/or smearing between different colored projections. For example black areas between the different colored projected entities may be utilized for differentiation of the entities. Optionally the black areas may facilitate reconstruction of a size (e.g. width for a color band) of the entities. Optionally the geometry of black areas separating entities is selected, to provide maximal coverage of the scene by the pattern entities (e.g. smaller black spaces and/or increased density of entities), and/or to facilitate crosstalk correction (for example reducing the density of entities and/or increasing the area of black spaces separating between entities).

In some embodiments, the different wavelengths are detected by different pixels of the imager (such as in a hyperspectral camera, e.g. IMEC SM4X4-470-630 CMOS), for example by covering the different pixels with interference filters that match the projected wavelengths.

In some embodiments, the different wavelengths are detected sequentially. Optionally, the different wavelengths are projected and/or detected sequentially. Optionally, a tunable filter is used for detecting the wavelengths sequentially.

In some embodiments, the pattern comprises a plurality of wavelengths or narrow wavelength bands (e.g. at least 5, at least 7, at least 15 or intermediate, higher or lower number). Optionally, the wavelengths are selected from a narrow spectral band. In some embodiments, projection of the narrow wavelength bands is implemented using interference filters applied to each pixel. In some embodiments, the wavelength range is selected according to available projection and imager technology (e.g. a range may be selected to fit a sensor for example 400-850 nm may fit a Si CMOS sensitivity). Alternatively or additionally, the range may be chosen according to properties of illuminated object (for example 400-700 nm may fit the visible range and/or provides higher contrast over the teeth). In some embodiments, the wavelength range is selected to increase contrast with the scanned teeth, for example a wavelength range selected from the shorter visible wavelength range (for example between 400-500 nm, 380-450 nm, and or 470-550 nm or intermediate, larger or smaller ranges). Additionally or alternatively, shorter wavelengths may be used, for example wavelengths of the ultraviolet range (e.g. shorter than 400 nm) are used.

A potential advantage of a pattern comprising a plurality of short wavelengths (or wavelength bands) selected from a relatively narrow spectral band may include lowering smearing of the intraoral features, improving color detection owing to the reduced crosstalk between wavelength channels. Another potential advantage may include reduced sensitivity for ambient light, contributing to a more accurate color identification. Accurate color identification may be effective to reduce ambiguities, which can cause errors in pattern restoration and/or errors in detection of depth variations in the scene.

Optionally, if the pattern comprises longer wavelengths (including for example non-blue colors for which there may be lower contrast and/or larger smear over the tooth), the pattern entities (e.g. stripes) are selected to be wider than those that would be used for the shorter wavelengths (purple-blue color range).

Various projection configurations and/or methods may be implemented for projecting the wavelength-coded pattern. For example, in some embodiments, a plurality of light sources (such as a plurality of LEDS or lasers) each configured for emitting light at a selected wavelength are arranged adjacent each other. Additionally or alternatively, a set of filters suitable for transmitting the selected wavelengths is attached to a light source (e.g. LED) for projecting the pattern onto the scene. Additionally or alternatively, a set of filters suitable for transmitting the selected wavelengths is attached to a transparent substance illuminated by a light source having a wider spectrum. Additionally or alternatively, a grating that diffracts light from a light source having a wider spectrum is used. Additionally or alternatively, a variable wavelength source such as a variable wavelength laser is used with a scanning mirror (e.g. MEMS mirror). Additionally or alternatively, a variable wavelength filter such as a variable interference filter is used for altering the transmitted wavelengths. Additionally or alternatively, the transmitted wavelength is changed in accordance with the varying wavelengths that are received in the sensor. Additionally or alternatively, the transmitted wavelength is modified according to the rolling movement of the sensor shutter, in a way that the camera detects different wavelengths in different areas of the scene as the shutter is moved over the scene.

An aspect of some embodiments relates to reducing crosstalk between imaged pattern entities by utilizing one or more separating regions in the pattern. In some embodiments, the separating regions comprise non-illuminated regions, defining dark regions between the pattern entities. In some embodiments, the dark regions enable separation of the pattern entities following scattering and/or smearing.

In some embodiments, a referential color pattern is projected onto the intra-oral scene. In some embodiments, the referential color pattern comprises colored entities and separation regions between entities of different colors. In an example, a referential color pattern comprises an arrangement of black and colored stripes arranged such that a black stripe separates between two colored stripes. Alternatively to a non-illuminated area, the separating region comprises a color which is not transmitted by a filter used at detection. Alternatively, frames with uniform lighting are acquired between frames with patterned lighting for extraction of color reflection properties of the scene. Additionally or alternatively, frames with uniform lighting are used for obtaining 3D information regarding matching features in the scene.

In some embodiments, the dark regions are large enough to avoid a geometrical overlap between imaged pattern entities. For example, in a pattern comprising dark regions in the form of stripes, the dark stripes are selected to be wide enough so as to ensure that for imaged pixels of at least a portion of the dark stripe (e.g. a vertical center thereof) a contribution of light from the colored entities is substantially nonexistent. Alternatively, a contribution of light from the colored entities exists, but other features (e.g. anchors) allow for identifying the dark region as such.

In some embodiments, detection of the referential pattern comprises subtracting the imaged color obtained in the black stripes situated at opposing sides of the colored stripe from the colored stripe, to reconstruct the colored stripe. Potential advantages of using the referential pattern may include reducing or preventing spectral crosstalk between the different stripes which may occur when the pattern light is scattered through the teeth, tissues and/or other oral contents. Scattering and/or smearing of the pattern entities may occur as a result of the different types of materials and/or structures in the intra-oral scene, for example teeth, fluids (e.g. saliva, blood), gum, artificial prostheses, treatment and/or food residuals, natural defects (e.g. cavities) and/or other. The smearing may be increased when the imaged surface is at a high angle to the sensor and/or when the focus of the sensor is reduced, for example due to parts of the surface being out of the preferred focus range of a sensor. For example, black areas may be increased to counteract increased smearing.

In some embodiments, one or more image processing algorithms such as spatial filtering, adaptive histogram equalization, local thresholding, non-maximum suppression, and/or other algorithms are applied to an imaged pattern that comprises dark regions for enhancement of the stripe's contrast, color, assessment of ridge location and/or other characteristics.

Use of dark separation regions may be especially advantageous when processing areas in which a distance between the stripes decreases, for example in areas exhibiting steep angles towards the imager.

An aspect of some embodiments relates to incorporation of one or more anchors in a pattern projected onto an intra-oral scene, by introducing irregularities in a structured light pattern. In some embodiments, the pattern comprises a monochromatic uniformly recurrent arrangement of stripes. In some embodiments, irregularities are introduced into the pattern instead of or in addition to multi-color information.

In some embodiments, the anchors are spread in the field of view to facilitate restoring the pattern from the acquired image. In some embodiments, restoring comprises indexing the imaged stripes of the pattern, by tracing each imaged stripe back to its matching counterpart in the known projected pattern. In some embodiments, the anchors are indexed directly, while the stripes are indexed according to their spatial location relative to the anchors. In particular, a structure of the stripe may be used for statistical analysis of relative location of the various points forming the stripe to the anchors. A potential advantage of using a structure of the stripe for analyzing location may include high sustainability to indexing errors caused by errors in evaluating a distance to the anchors, caused by stripe loss in the imaged scene. Stripe loss may be caused by the scene geometry, shadows in the scene, tooth defects, operator movement and/or other factors or combinations thereof.

In some embodiments, the amount of anchors incorporated in a pattern is selected in accordance with the scene variability, for example, if the scene comprises a relatively small amount of smooth patches (a smooth patch being defined as a region having no depth discontinuities), a reduced amount of anchors (e.g. as compared to a scene with a higher number of smooth patches) can be used. For example, a recurrent stripe pattern can be used, with an anchor spread selected to ensure that at least one anchor is situated upon a smooth patch. Once that anchor is indexed, the stripe portions situated within the same smooth patch allow for expanding of the indexing to additional detected points of the pattern.

In some embodiments, the anchors are in the form of diagonals intersecting the stripes, forming a plurality of junctions (between the stripes and the diagonal) that can be used as anchors. In some embodiments, anchors are provided in the form of two or more color zones. Other examples of anchors may include variations between the stripes, such as variations in width, spacing, shape, angle, color and/or other variations or combinations thereof. Other variations may include in-stripe variations, for example a stripe width that changes along the stripe, missing portions along the stripe, and/or other in-stripe variations. In some embodiments, anchors (e.g. in the form of stripe variations) are located, for each stripe, at a different horizontal position relative to variations of one or more adjacent stripes, to facilitate identifying the stripes.

An aspect of some embodiments relates to scanning an intra-oral scene using unstructured lighting and patterned lighting. Optionally, the unstructured lighting comprises uniform lighting. Additionally or alternatively, the unstructured lighting comprises lighting in which no predefined pattern is projected.

In some embodiments, information obtained by imaging the scene using unstructured lighting facilitates restoring the pattern from an image obtained under patterned lighting, or vice versa. Some embodiments comprise interchanging between an unstructured lighting frame and a patterned frame. In some embodiments, information obtained by imaging the scene using unstructured lighting facilitates restoring the pattern from an image obtained under patterned lighting. For example, an image obtained under unstructured lighting can be used for collecting and/or completing information about the intra oral scene, for classifying the imaged content. Another possible usage of unstructured lighting is detecting cues of, depth discontinuities in the scene, which define the borders of the smooth patches. In another example, the image obtained under unstructured lighting is used for natural coloring of the scene. In another example, the image obtained under unstructured lighting is used for evaluating reflection characteristics of the different materials and/or structures in the scene. In some embodiment, the unstructured lighting is white. Alternatively or additionally, reflection characteristics of the different materials and/or structures in the scene are evaluated at the different spectral regions and/or multiple spectral regions, for example RGB.

In some embodiments, areas in the scene that are prone to projected stripes loss are detected. Optionally, signal-to-noise evaluation methods are applied to the unstructured light image and/or patterned image to mask these areas. In some embodiments, contrast enhancement techniques are applied upon the combination of patterned and unstructured light images.

In some embodiments, the transmission power (of either structured and/or unstructured light) is modified during scanning. In an example, the power is adjusted after one or more images are acquired and it can be estimated whether higher or lower power is needed. Optionally, the estimation is performed according to the signal to noise ratio and/or according to the saturation level of the received color.

In some embodiments, pre-defined power levels are used; additionally or alternatively, the power levels are dynamically adjusted during scanning, e.g. based on the acquired images. Optionally, power levels are set in accordance with the wavelength ranges used and/or selected per different areas in the field of view.

It is noted that a "wavelength" as referred to herein may include a single wavelength or a range of wavelengths, such as a narrow band of wavelengths. A "color" as referred to herein may contain a single wavelength, a narrow band of wavelengths or a mixture of wavelengths.

Referring now to the drawings, FIG. 1 is a flowchart of a method for scanning an intra-oral scene by projecting a multi-wavelength pattern and separating the different wavelengths upon detection of the pattern, according to some embodiments of the invention.

In some embodiments, a dentist and/or other clinical personnel decide to perform a dental measurement using an intra oral scanner (IOS) (100). In some embodiments, measurement is performed for further construction of a dental prosthetic such as a crown, bridge and/or other dental structures. In some embodiments, a 3D measurement of a portion of a tooth, a full tooth, a plurality of teeth and/or partial or full dental arch is acquired. Optionally, for example for construction of a prosthetic that extends below the gum stripe, measurement below the gum stripe is carried out. In some embodiments, a measurement of a non-visible area such as a subgingival area is obtained.

In some embodiments, the intra-oral scene is illuminated by a multi-wavelength pattern (102). In some embodiments, the pattern comprises a recurrent arrangement of entities, for example a recurrent sequence of stripes. In some embodiments, one or more stripes of the pattern are each comprised of a narrow band of wavelengths. Optionally, the FWHM of such narrow band is 1 nm, 5 nm, 10 nm or intermediate, longer or shorter widths. In some embodiments, one or more stripes of the pattern are absent of light, defining black regions in the pattern.

In some embodiments, the projected pattern comprises at least 2 wavelengths, at least at least 5 wavelengths, at least 7 wavelengths, at least 10 wavelengths, at least 20 wavelengths or intermediate, larger or smaller number.

In some embodiments, an image of the illuminated scene is captured (104) using a light collector such as a camera and/or imager of the IOS.

In some embodiments, the imager is configured for selectively detecting the plurality of wavelengths in the pattern (106). In some embodiments, the imager comprises a filter suitable for transferring wavelengths of interest. In some embodiments, the wavelengths transferred by the filter are selected in accordance with the different wavelengths of the projected pattern and/or selected in accordance with the imaged area. In some embodiments, the filter is configured to transfer two or more wavelengths that are selected in accordance with their relative spatial location on the pattern, for example configured to transfer at least one wavelength from an upper region of the pattern and at least one wavelength from a lower region of the pattern.

In some embodiments, the received signals are filtered by an interference filter, a dichroic filter, a liquid crystal filter and/or other filter designed for transmitting selected wavelengths of the pattern and blocking others.

In some embodiments, only a single pattern is projected throughout the scanning process. Optionally, only power settings and/or filter settings (of a transmitting and/or receiving filter) are modified throughout the scanning process, while the pattern remains constant. A straightforward advantage of using a single pattern may include reducing processing errors which may occur as a result of movement of the system in between subsequent frames. Another potential advantage of projecting and detecting a single pattern may include simplifying use. Another potential advantage may include providing for an IOS having a relatively small form factor due to a simple projector structure, for example as compared to an IOS that projects multiple patterns. A small form factor scanner for example as described herein may be especially advantageous for accessing hard to reach areas in the mouth, for example for obtaining a measurement of a tooth close to or at the gum stripe, where a steep angle between the tooth wall and the scanner may be present.

Alternatively, a plurality of patterns such as 2, 3, 5, 7 or intermediate or larger number of patterns is projected.

Optionally, the intra-oral scene is illuminated with unstructured lighting (108), e.g. uniform lighting, and the unstructured light image is then captured (110). In some embodiments, the scene is illuminated by an interchanging sequence of unstructured lighting and patterned lighting and/or any other sequence of unstructured lighting and pattern lighting (for example, 1 frame of unstructured lighting followed by 2 frames of patterned lighting, 1 frame of unstructured lighting followed by 3 frames of patterned lighting, 2 frames of unstructured lighting followed by 1 frame of patterned lighting and/or other combinations). Optionally, information gathered from the unstructured light image is used for constructing the 3D model of the scene. Optionally, information gathered from the unstructured light image provides cues for restoring a pattern, for example indications of areas prone to stripe loss.

In some embodiments, a 3D model of the scene is constructed (112). In some embodiments, the model is constructed by restoring the projected pattern. In some embodiments, restoring includes a calculation based on a shift of the projected pattern entities when striking surfaces of the scene, the shift being parallel to the baseline connecting the centers of the projector and the optical aperture of the camera.

Pattern distortion may be affected by one or more of the varying surface shape of the scene, the plurality of structures in the scene (e.g. teeth, gum, prosthetics), the plurality of materials in the scene and their different reflective properties (e.g. dentin, enamel, artificial fillings, soft tissue, saliva), and/or other factors.

In some cases, the projected pattern entities are smeared, for example by the contents of the intra oral scene such as teeth, gums and/or other tissue. Smearing may induce optical crosstalk between the imaged pattern entities.

In some embodiments, selective detection of the different wavelengths in the pattern is effective to reduce the spatial crosstalk. Optionally, filtering is performed to reduce crosstalk.

In some embodiments, as mentioned hereinabove, information from one or more images of the scene obtained under unstructured lighting (e.g uniform lighting) is used for constructing the 3D model. Optionally, information from unstructured light images is used for reconstructing the imaged pattern. In some embodiments, the unstructured light image is used for natural coloring of the model. Additionally or alternatively, reflection properties of objects in the scene and/or reflection properties at different locations in the scene are exploited from the unstructured light image. Additionally or alternatively, geometry cues of the scene (e.g. depth information, such as locations of depth discontinuities) are extracted from the unstructured light image. In some embodiments, pixel by pixel analysis, global analysis, and/or other processing methods are applied to the unstructured light image to extract the information. In some embodiments, information obtained from the unstructured light image is used for removing local spectral reflectance effect and/or local color of the target.

In some embodiments, unstructured lighting and patterned lighting are projected simultaneously, for example via two channels. A potential advantage of projecting both light schemes simultaneously may include reducing effects of scanner movement, such as due to user hand movement, on the acquired images.

Figure 2:
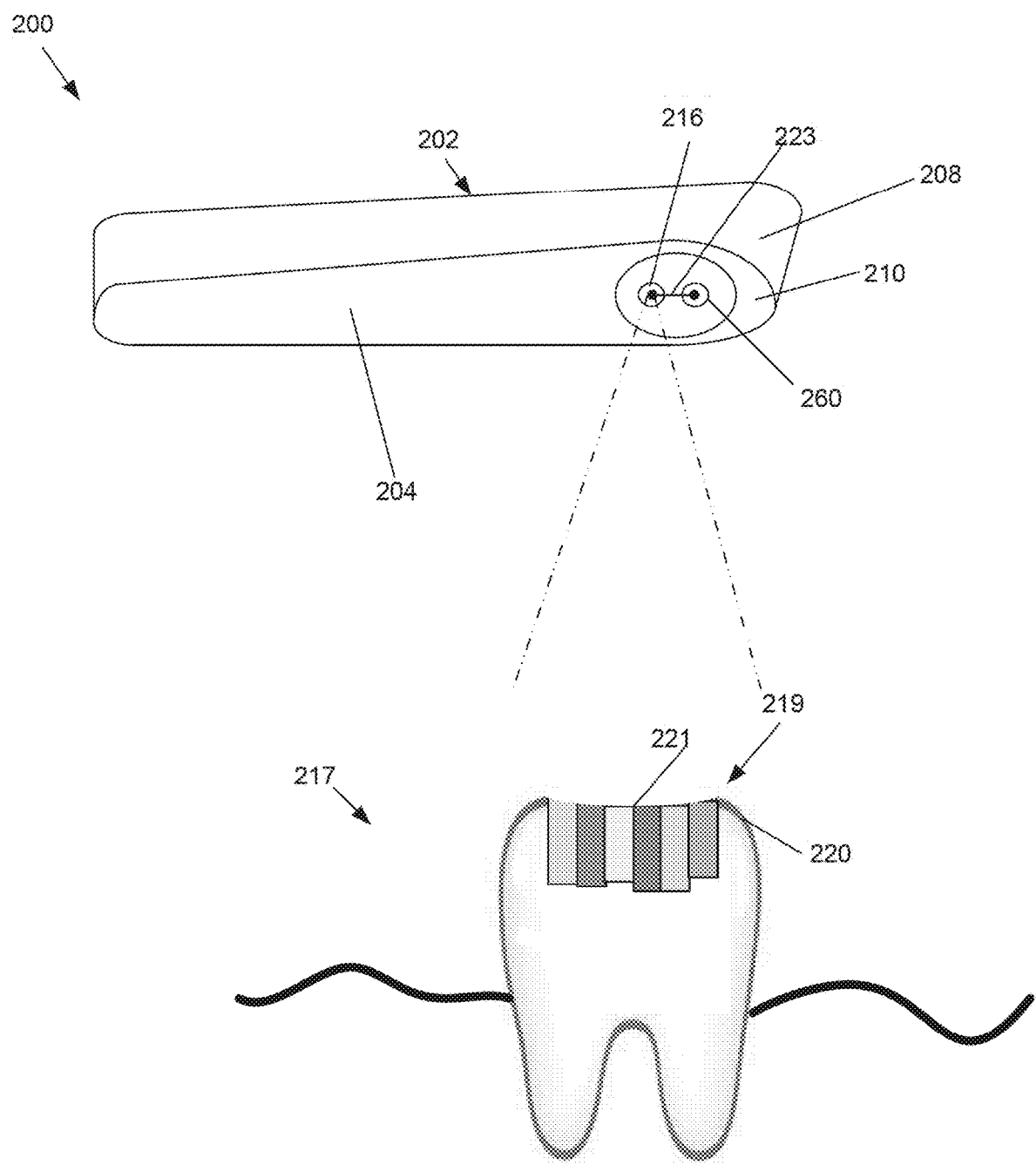
FIG. 2 is a schematic illustration of a 3D intra-oral scanner system, according to some embodiments of the invention.

FIG. 2 is a schematic illustration of a 3D intra-oral scanner system, according to some embodiments of the invention.

In some embodiments, IOS system 200 comprises an IOS 202, shaped and/or sized for insertion into the mouth for scanning an intra-oral scene 217.

In some embodiments, IOS 202 includes a hand piece 204 and a head portion 208. In some embodiments, an oral-facing surface 210 of head portion 208 includes a light emitter, pattern projector 216, and an optical aperture of a camera or imager 260.

In some embodiments pattern projector 216 may include any suitable light source, such as a light-emitting diode (LED), a laser, such as edge emitter or VCSEL etc. Pattern projector 216 optionally includes beam shaping optics, such as a lens, for example to use the light source light efficiently. In some embodiments, optical fibers with a remote light source may be used.

In some embodiments, pattern projector 216 and/or a different light projector is configured for projecting a pattern 219 onto the chosen surface, for example onto a surface of tooth 220. In some embodiments, pattern 219 comprises an arrangement of recurrent parallel stripes 221. In some embodiments, each stripe 221 is composed of a different wavelength or wavelength range. Optionally, the pattern is composed of a total of 3 wavelengths, 5 wavelengths, 7 wavelengths, 10 wavelengths, 20 wavelengths or intermediate, larger or smaller number of wavelengths or narrow wavelength bands. In to some embodiments, pattern projector 216 comprises a plurality of interchanging sub-sources, for example a light source suitable for projecting patterned lighting and a light source suitable for projecting uniform lighting.

In some embodiments, wavelengths of the pattern are selected from the visible wavelength range. Optionally, the wavelengths are selected from the lower end of the visible range, for example between 400-500 nm, or intermediate, higher or lower ranges (for example between 400-500 nm, between 380-420 nm, between 460-550 nm, between 350-450 nm). A potential advantage of selecting wavelengths from the lower end of the visible range may include maximizing contrast when scanning teeth [for example as mentioned herein above]. Also, wavelengths of the lower end of the visible range may be easily observed on the gingiva. Additionally or alternatively, the pattern includes a combination of wavelengths from the visible range and other regions of the electromagnetic spectrum, e.g. wavelengths of the IR range and/or UV range.

In some embodiments, stripes 221 are generally perpendicular to line 223 (further referred to herein as "baseline") which extends between an optical aperture of pattern projector 216 and an optical aperture of the imager 260. Additionally or alternatively, one or more stripes 221 are at an angle to line 223, for example an angle of 5 degrees, 10 degrees, 20 degrees, 30 degrees or intermediate, larger of smaller angles.

In some embodiments, the IOS comprises one or more folding mirrors positioned to redefine the baseline by forming virtual aperture locations.

In some embodiments, imager 260 comprises one or more filters for selectively detecting the different wavelengths of pattern 219. Optionally, the filters are narrowband filters.

In some embodiments, the filters are configured to detect different wavelengths at different areas of the scene.

In some embodiments, filter properties are modified during scanning (e.g. using mechanical and/or electrical means), for example so that the filter transfers a wavelength or a set of wavelengths different from a currently transferred set of wavelengths.

In some embodiments, the different wavelengths are detected by different pixels of the imager, for example by covering the pixels of the imager with interference filters that match the projected wavelengths, for instance as in a hyperspectral camera.

In some embodiments, the plurality of wavelengths are projected and/or detected sequentially over time. Optionally, sequential detection is achieved using a scanning interference filter and/or other tunable filter.

Figure 3:
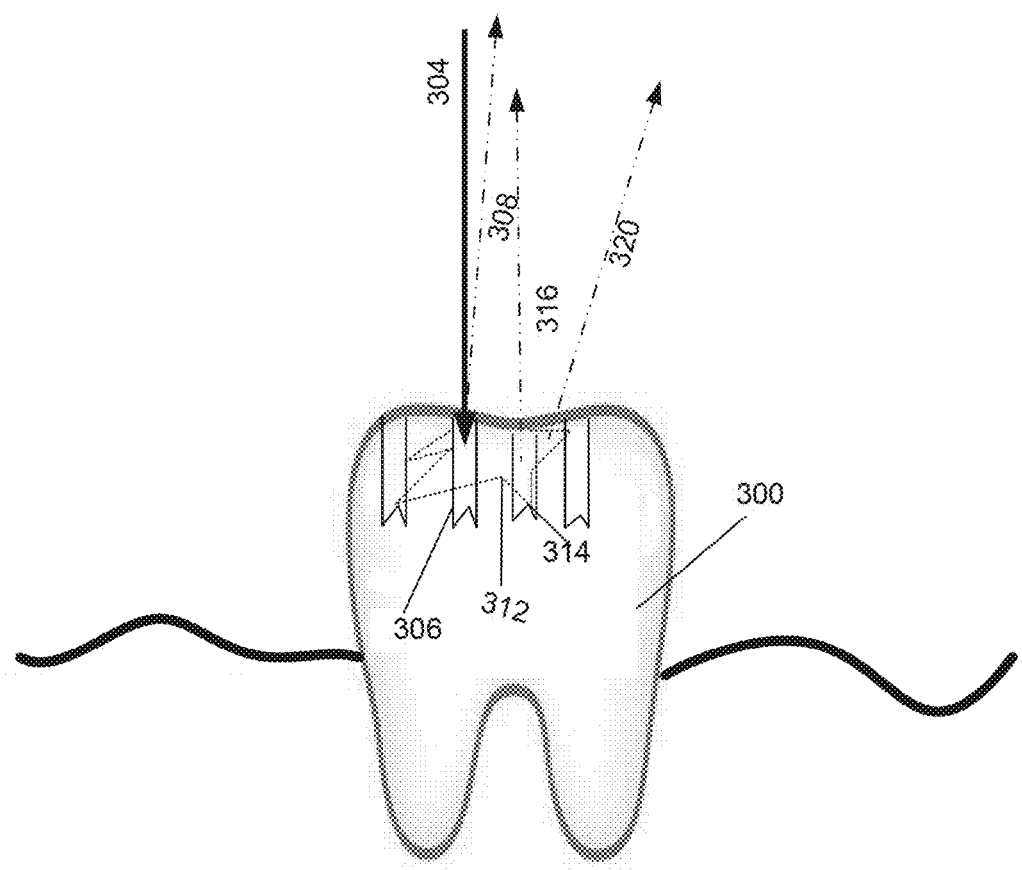
FIG. 3 schematically illustrates interaction between projected light and the tooth and/or other oral content, according to some embodiments of the invention.

FIG. 3 schematically illustrates interaction between projected light and objects in the intra-oral scene, such as teeth and/or gums.

In some embodiments, tooth 300 is illuminated by an IOS for example as described hereinabove) and/or using other light-projecting modality with a multi-color stripe pattern. In some embodiments, at least some of the projected light photons (indicated by arrow 304) that illuminate a stripe such as stripe 306 are reflected back from the tooth (as indicated by arrow 308) and received by the IOS. Additionally or alternatively, at least some of the projected light photons undergo scattering 312 by the tooth and are at least partially absorbed in the tooth and/or are travel a certain depth into the tissue and/or are reflected from tooth portions different from the tooth portion onto which the stripe was projected. For example, light photons (indicated by arrow 316) may be returned from a location of an adjacent stripe 314, where they may interfere with back-reflected photons of stripe 314 which is colored differently than stripe 306, thus reducing the probability of correctly identifying the color of stripe 314. Additionally or alternatively, light photons (indicated by arrow 320) return from an in-between stripe location. Optionally, these scattered light photons returning from a non-illuminated, in-between stripe location are used during detection as a reference for correctly identifying the color of stripe 314.

In some embodiments, the color of the non-illuminated regions (e.g. a non-illuminated region alongside a colored stripe) is used during image processing for determining the projected color of the stripe. An exemplary method for determining the stripe color comprises subtracting the color received at the non-illuminated regions from the colored stripe. A potentially more accurate example is subtraction of a weighted average of the not illuminated region, wherein weights are set, for instance, according to the distance from illuminated regions. Optionally, processing is performed for each color channel separately (e.g. for each of the RGB channels). Another exemplary method comprises estimating a scattering factor of the local material (e.g. tooth or gums) and removing the scattering accordingly, for instance using linear relation coefficients that depend on the scattering factor of the material. Optionally, the contribution of ambient illumination is taken into consideration as well. Another exemplary method comprises using a local spatial filter to subtract background color obtained using the non-illuminated regions.

In some embodiments, the intensity of light returned from different locations of tooth 300 may decrease as the distance between the location from which the light is returned and the point of incidence of the projected light with the tooth increases. Another factor which may affect the intensity of the returning light may include the reflection coefficient of a material and/or composition of materials from which the light is returned. The factor by which the intensity is reduced may depend on material composition, surface and/or volume features of the tooth. In some embodiments, one or more materials in the scene are identified according to their reflection factor.

Figure 4A:
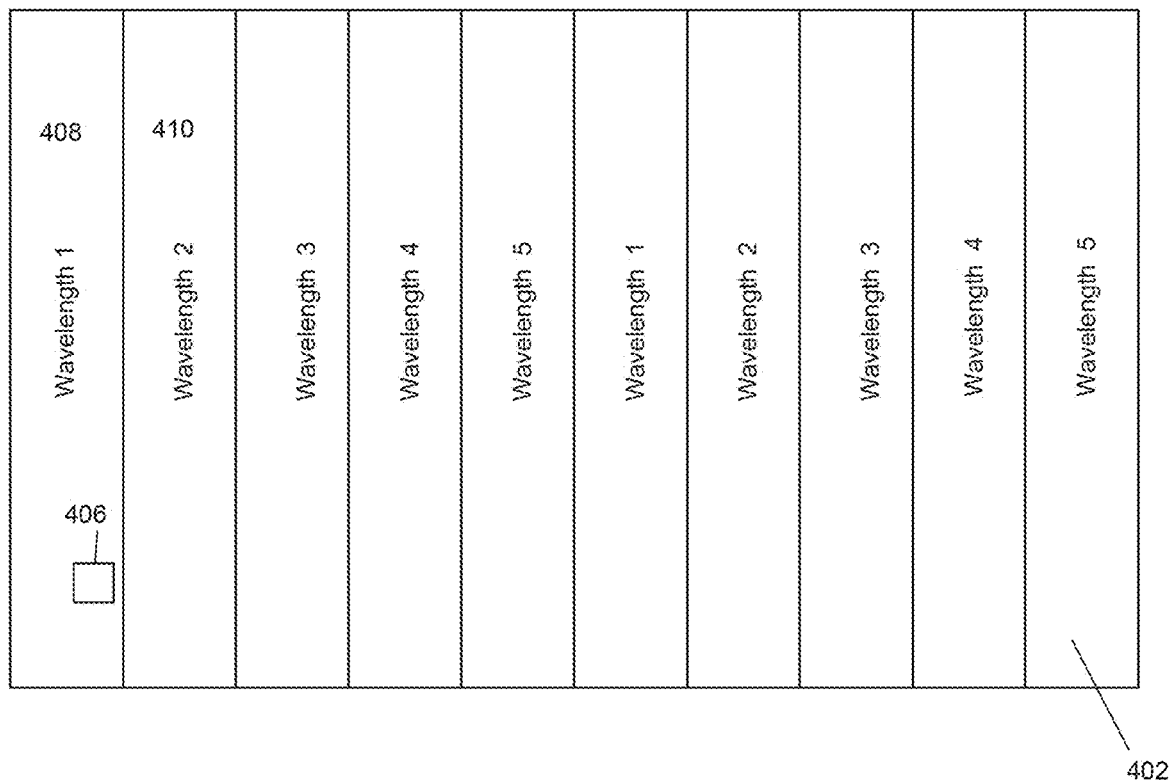
FIGS. 4A-B are an example of a multi-wavelength pattern for projecting onto an intra oral scene (FIG. 4A), and a schematic spectral graph of an exemplary pixel of the image (FIG. 4B), according to some embodiments of the invention.
Figure 4B:
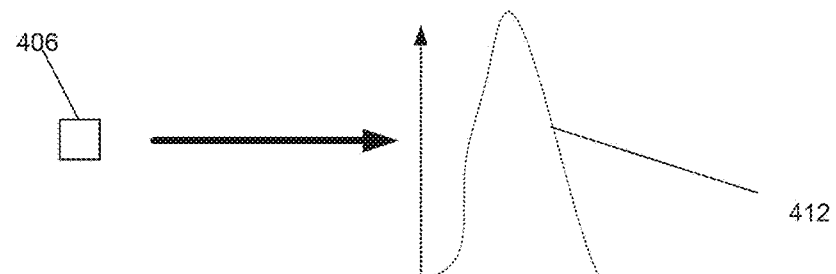

FIG. 4A is an example of a multi-wavelength pattern for projecting onto an intra oral scene, according to some embodiments, and FIG. 4B schematically illustrates a spectral graph of an exemplary pixel of the image, according to some embodiments.

In some embodiments, pattern 400 comprises an arrangement of colored stripes 402. In some embodiments, each colored stripe contains a narrowband wavelength range. In some cases, narrowing the spectral bandwidth of pattern entities (especially of adjacent and/or neighboring entities) may reduce spectral crosstalk. In some embodiments, narrowband pattern projection is combined with narrowband pattern detection (e.g. hyperspectral camera). In some embodiments, combination of narrowband projection and detection with low spectral crosstalk between pattern features may further reduce crosstalk and/or improve accuracy of reconstructed projected pattern features colors and/or locations. Reducing crosstalk may facilitate accurate reconstruction from a strongly smeared image (i.e. spatial smear). For example, reducing crosstalk may facilitate more accurate measurement of a projected pattern on translucent teeth and/or crowns. Reducing crosstalk may facilitate accurate reconstruction of spatial patterns smeared by the limited depth of field (e.g. defocus) of short working distance high resolution optical systems and/or by a combination of the above factors.

In some embodiments, the total number of wavelengths in the pattern is, for example, at least 2 wavelengths, at least 5 wavelengths (for example as shown herein), at least 7 wavelengths, at least 16 wavelengths, at least 25 wavelengths or intermediate, larger or smaller number.

In some embodiments, detection of pattern 400 by the IOS comprises filtering the received light, selectively transmitting the predetermined wavelengths of the pattern (e.g. wavelengths 1-5) and reflecting and/or absorbing others. Optionally, a tunable filter is used, enabling adjustment of the selected wavelengths.

In some embodiments, filtering of the received signals at detection of the imaged pattern is effective to reduce spectral crosstalk such that at an exemplary pixel 406 of a stripe of interest (in this example, stripe 408 of wavelength 1) there is no significant contribution of an adjacent stripe (in this example, stripe 410 of wavelength 2) and/or of more distant stripes. For example as shown in FIG. 4B, in the spectra graph of pixel 406, due to the use of interference filters for the different channels, the contribution of wavelength 2 to the amplitude 412 of pixel 406 would be smaller than 20%, 10%, 5% or intermediate, larger or smaller values. In some embodiments, wavelength bands of adjacent entities are selected to include wavelengths that are relatively far apart from each other on the spectral range. Such arrangement may further reduce spectral crosstalk between the entities.

Figure 5A:
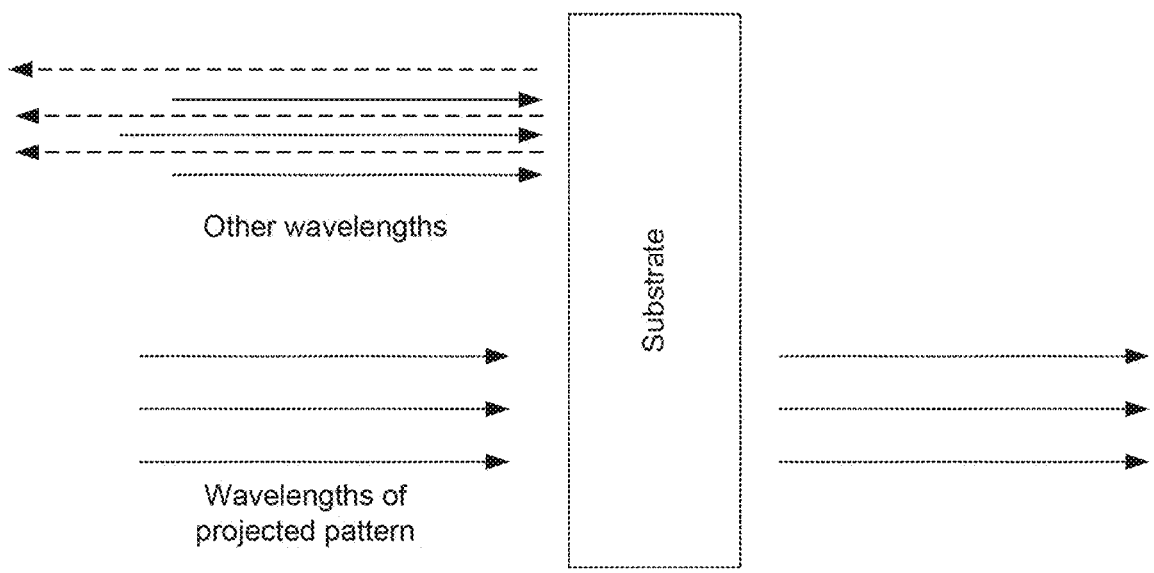
FIGS. 5A-B schematically illustrate transmission of filters used at detection of the pattern, according to some embodiments of the invention.
Figure 5B:
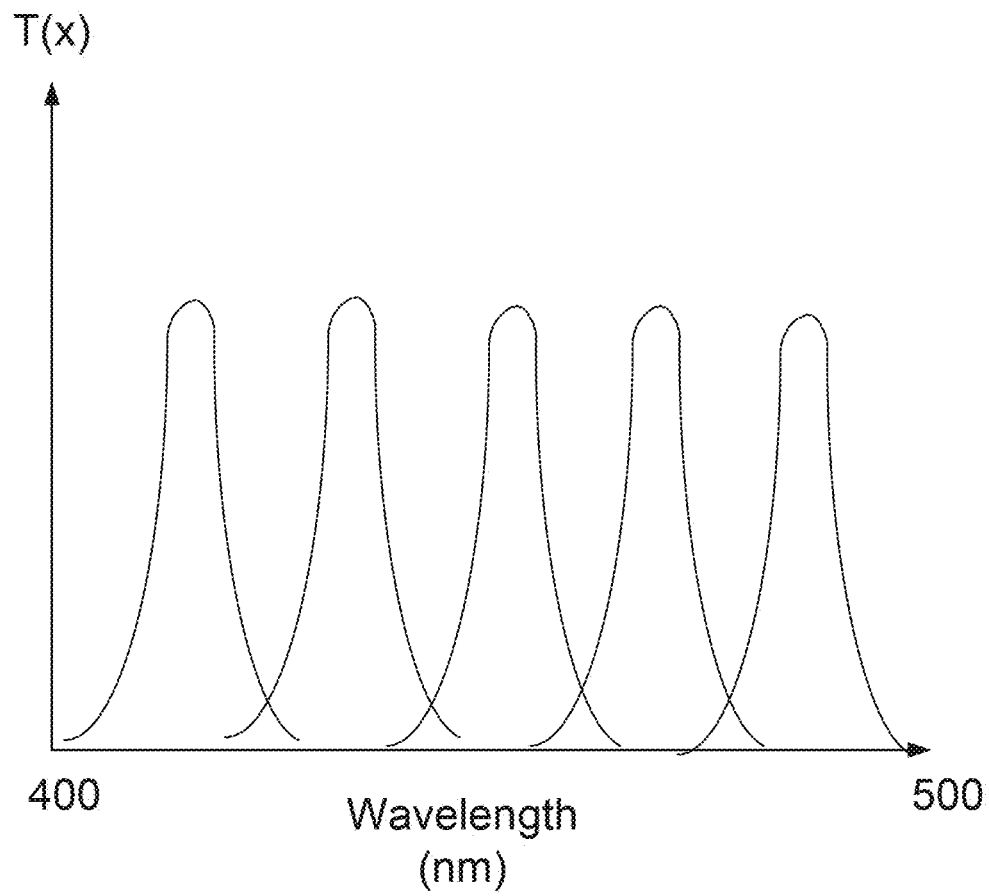

FIGS. 5A-B schematically illustrate transmission of filters used at detection of the pattern, according to some embodiments of the invention.

In some embodiments, the IOS imager comprises one or more filters suitable for transmitting selected wavelengths and/or wavelength ranges of interest, for example as commonly used in hyperspectral cameras. FIG. 5A schematically illustrates passing of selected wavelengths, and blockage (e.g by reflection) of wavelengths that are not of interest. FIG. 5B schematically illustrates transmission efficiency of the filters used at detection, in this example including 5 different narrowband filters configured for transmitting 5 selected wavelengths, for example wavelengths between 400 and 500 nm on the same graph.

In some embodiments, a filter is configured to dynamically transfer a selected wavelength at times that are synced with projection of the specific wavelength.

In some embodiments, different pixels of the imager comprise different filters, for example such that a fraction of the pixels of the imager (e.g. ⅓, ⅕, ⅛ or intermediate, larger or smaller fraction) will receive a specific wavelength out of the plurality of wavelengths. For example, 1/5 of the pixels of the imager are configured to receive a single wavelength out of a total of 5 different wavelengths.

In some embodiments, pixels configured to capture a specific wavelength also capture a small amount of one or more other wavelengths. Optionally, such capturing method provides for producing a high dynamic range (HDR) image.

In some embodiments, a spectral band will be selected due to a property of interaction between the band and an intra oral object. For example, the five bands of FIG. 5B are all in the high frequency violet-blue-green visible spectrum. These bands may be scattered less by teeth as compared to lower frequency bands (for example red and/or yellow bands).

In some embodiments, narrow spectral bands are selected with very small overlap. For example, the spectral bands in FIG. 5B have pass bands of less than 10 nm and/or transition bands of less than 10 nm. Optionally there is very little overlap between bands, for example overlap between bands in FIG. 5B is restricted to the stop band of the color bands. For example the sensitivity of overlapping (spectral cross talk) is at most 1/10 the sensitivity to the pass band of the filter.

In some embodiments, the sensitivity of a sensor is increased by increasing the width of a passband. Optionally the specificity of the sensor may be increased by decreasing the width of the pass band. Optionally cross talk may be decreased by decreasing the overlap of bands, for example by decreasing the combined width of the pass band and the transition band.

FIGS. 6A-F are various configurations for projecting a multi-wavelength pattern onto an intra-oral scene (shown at a side view), according to some embodiments.

Figure 6A:
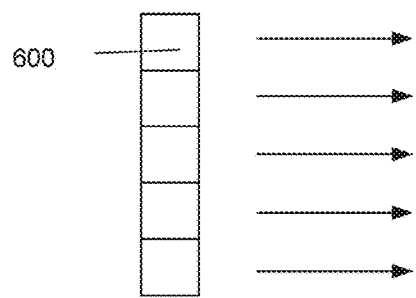
FIGS. 6A-F are various configurations for projecting a multi-wavelength pattern onto an intra-oral scene, according to some embodiments of the invention.

In some embodiments, projection of the wavelength coded pattern comprises using a plurality of light sources, each configured to illuminate the scene with one of the wavelengths of the pattern. For example, as shown in FIG. 6A, a plurality of LEDs 600 are arrayed adjacent each other. Optionally, LEDs used for display technologies such as AMOLEDs are used. In some embodiments, independently operable LEDs are arranged in a dense matrix. Optionally, AMOLEDs formed as thin elongated blocks are used.

Figure 6D:
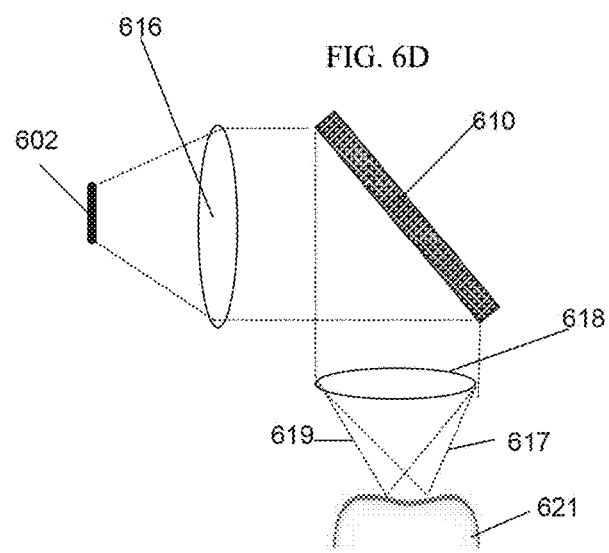
Figure 6C:
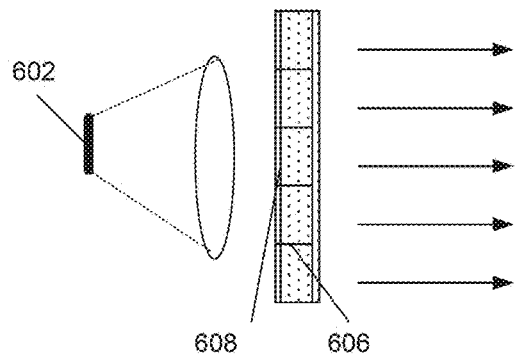
Figure 6E:
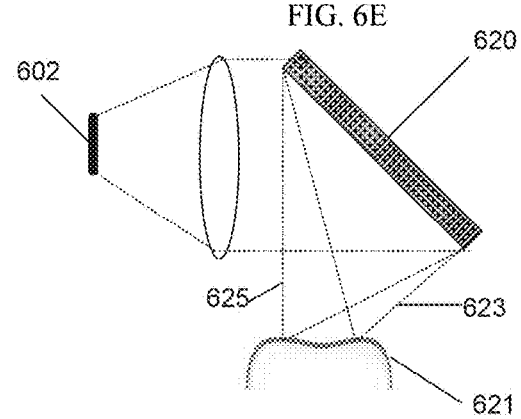
Figure 6F:
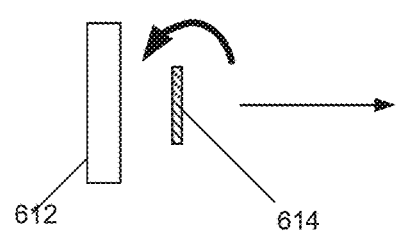
Figure 6B:
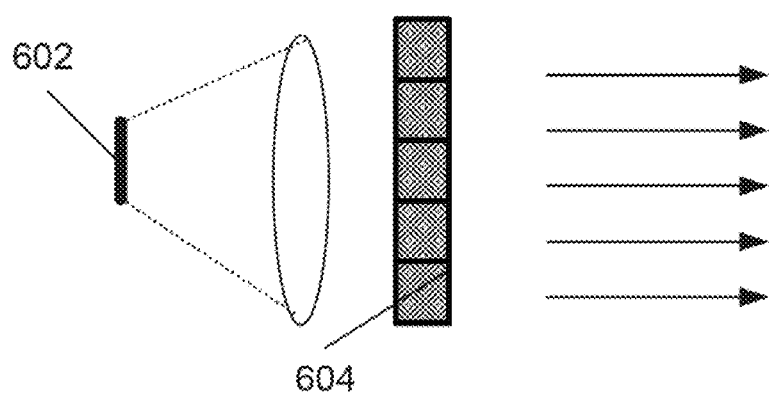

Additionally or alternatively, for example as shown in FIG. 6B, a light source 602 having a wider spectrum is used in conjunction with one or more filters 604. Optionally, for example as shown in FIG. 6C, a set of interference filters 606 attached to a transparent substance 608 is illuminated by light source 602 having a wider spectrum. In some embodiments, dark areas are produced by adding a transparent blocking mask (e.g. chrome coated glass) on top of the a filter substrate and/or by attaching an adjacent mask to a lower resolution color filters pattern. An optional advantage of such embodiments that high resolution chrome masks (e.g. <1 um resolution) can be produced at relative low cost and can provide the needed resolution while the color filters, may more difficult to produce with high resolution, can be produced at lower resolution and the combination will still have high resolution.

Additionally or alternatively, for example as shown in FIG. 6D, a grating 610 that diffracts light from a light source 602 having a wider spectrum is used for projecting the pattern. In some embodiments, a first lens 616 is configured to collimate the light projected by light source 602. In some embodiments, a second lens 618 is positioned to direct the different wavelengths such as wavelengths 617 and 619 leaving grating 610 onto the different locations of the intra-oral surface, such as onto a surface of tooth 621.

Additionally or alternatively, for example as shown in FIG. 6E, a diffractive optical element 620 is positioned to diffract the light projected by light source 602 and optionally to direct the different wavelengths such as wavelengths 623 and 625 towards the intra-oral surface, such as onto a surface of tooth 621. Diffractive optical element 620 may be configured to produce the effect of one or more lenses and a grating.

Additionally or alternatively, for example as shown in FIG. 6F, a variable wavelength source 612 is used. For example, a tunable laser is used with a 1D scanning mirror 614 (such as a MEMS mirror). Additionally or alternatively, other optical components suitable for directing or re-directing light are used.

Additionally or alternatively, a wide spectrum light source is used with a scanning mirror (and/or other light re-directing component) to redirect light to a dynamically changing filter.

Other color projection configuration may include a glass cover having the different colors, for example in the form of stripes and/or squares. Optionally, colors that highly contrast the tooth are used (such as blue and/or purple). Optionally, the glass cover is attached to a light source such as a LED, along with micro lenses.

In some embodiments a light projector includes a mask. For example, the mask is used to give a geometric form to an illumination entity. Additionally or alternatively, a filter is combined with a monochrome mask (e.g. chrome on glass). For example, a high resolution mask may be combined with a low resolution color filter (e.g. diachronic filter, photographic transparency, low resolution interference pattern) to produce high resolution color entities.

Figure 7:
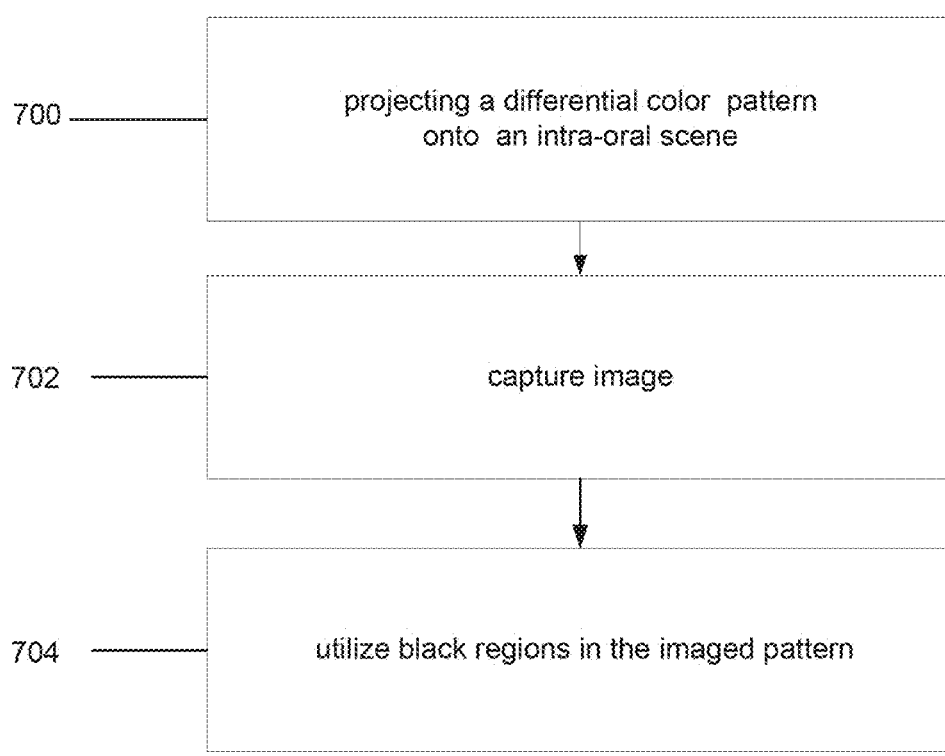
FIG. 7 is a flowchart of a method for scanning an intra-oral scene using a referential color pattern, according to some embodiments.

FIG. 7 is a flowchart of a method for scanning an intra-oral scene using a referential color pattern, according to some embodiments.

In some embodiments, a referential color pattern is projected onto the intra-oral scene (700). In some embodiments, the referential color pattern comprises colored entities such as stripes, wherein two colored stripes are separated from each other by a separating region such as a black region. Optionally, the separating region is in the form of a stripe. In some embodiments, the separating region is a non-illuminated region. Such configuration may be advantageous when the number of wavelength bands of the imager is limited and crosstalk between the different bands is significant, for example when an RGB imager with a Bayer filter for sensing the patterned light is used. Alternatively, the separating region is illuminated with a wavelength substantially different from the wavelengths of interest of the pattern, so that at detection the differently colored separating region can act as reference.

In an example, a first stripe comprises a blue color; a second adjacent stripe comprises a green color; and a separating region between these stripes is black. In another example the separating region between stripes is illuminated with radiation that is easily differentiated from the stripes. For example, a separated region may be illuminated with NIR wavelength radiation. Optionally, the illumination in the dark area may be used to image the "dark area" with little or negligible effect on the detection of an optical entity. For example, dark areas may be imaged in NIR without significant crosstalk affecting stripes in the visible range. Alternatively, the separating region comprises a color of a substantially different wavelength, a plurality of different wavelengths or wide spectrum light.

In some embodiments, the image of the pattern-illuminated scene is captured (702), for example using an imager such as described hereinabove. In some embodiments, the captured image is processed to restore the pattern.

Some embodiments comprise utilizing the black regions in the imaged pattern (704) for restoring the pattern and/or for reducing crosstalk. Optionally, color reconstruction is performed by subtracting measurement of the light that returns from what was projected as black regions located at opposing sides of the colored stripe of interest, from measurements of the colored stripe of interest. A potential advantage of using the non-illuminated stripes of the pattern may include robust color reconstruction of the color stripes, which is less or not affected by optical smear and/or scattering, as the black regions act to separate between the neighboring colors and provides for removal of background scattered light, such as of light scattered within the tooth In some embodiments, detection of the referential pattern is performed using an RGB Bayer filter. Alternatively, a filter suitable for transferring a different number of wavelengths (e.g. 5, 7, 10, or intermediate, larger or smaller number of wavelengths) is used for detection. Optionally, a tunable filter is used.

In some embodiments, additional local and/or global preprocessing of the pattern is applied, for example for enhancing the pattern stripes.

Figure 8:
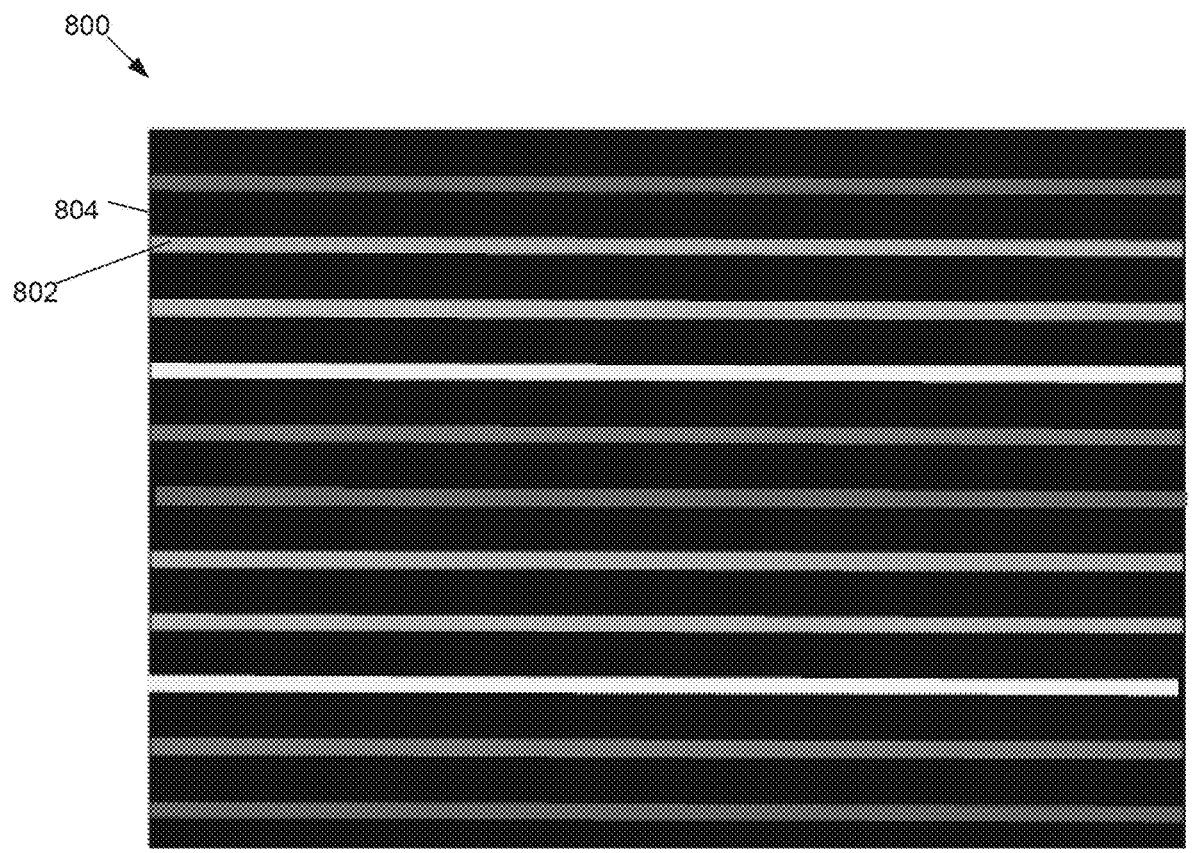
FIG. 8 is an example of a referential color pattern, according to some embodiments of the invention.

FIG. 8 is an example of a referential pattern 800, according to some embodiments. Optionally, an oral space is illuminated with a pattern 800 that comprises 7 different colors of pseudo random sequence. Optionally, each colored stripe 802 in pattern 800 is one third the width of an intervening black region 804.

In some embodiments, pattern 800 comprises at least 3, at least 5, at least 7, at least 10, different colors or intermediate, larger or smaller number of colors. In this example, a recurring sequence of 5 different colors is used. (The colored stripes are shown in this figure in grayscale but it is noted that various colors (e.g. red, green, blue, purple, yellow) and/or combinations thereof can be used). In some embodiments, a pseudo-random sequence (for example of 7 colors) is used. In some embodiments, pattern 800 is arranged such that each colored stripe 802 is located intermediate two black regions 804, extending parallel to the colored stripe. For example, pseudo random sequence of different colors is used. In some embodiments, pattern 800 is may have different geometrical patterns of illuminated areas and/or dark areas. Optionally, some illuminated areas may be separated by dark regions of varying sizes and/or shapes. Alternatively and/or additionally, some illuminated areas may be adjacent to one another. For example, where illuminated areas can be accurately separated by other aspects (e.g. spectral differentiation), smaller or no intervening dark areas are used.

In some embodiments, a width of a black region (e.g. stripe) is selected to be 0.5, 1, 2, 3, 5, or intermediate, larger or smaller times a width of the colored stripe.

Optionally, the width of the black region is selected to be large enough to enable color separation in the detected image, after the projected pattern was smeared by the surface of the tooth and/or by other intra-oral contents. Optionally, the width of the black region is selected to be large enough to enable geometrical separation between neighboring colored stripes, especially when the projected pattern is reflected back from a steep area in the scene which may effectively reduce the distance between the colored lines in the detected image.

In some embodiments, a thickness of the black stripe is selected to produce 0.3, 1, 5, 10, 30 or intermediate, higher or lower number of pixels on the detector when the pattern is projected on a surface located a known distance from the imager.

In some embodiments, a width of the black stripes and/or colored stripes varies between stripes.

In some embodiments, the sequence of the colors is selected to maximize the distance between the colors in the color space of the detector.

For example, if the detector is an RGB detector and the colors are selected from the Red Green and Blue colors a color comprising Red and Green would be placed near a color comprising Blue only so the distance in the color space will be maximal, such as between (1,1,0) and (0,0,1).

In some embodiments, by using a predefined color sequence, the color of a detected stripe can be determined according to the known color of one or more adjacent stripes.

In some embodiments, the colors and/or the sequence of the colors is selected to be suitable for use with color spaces other than the RGB cube color space, such as HSL, HSV, CMY, CMYK and/or other color spaces.

Figure 9:
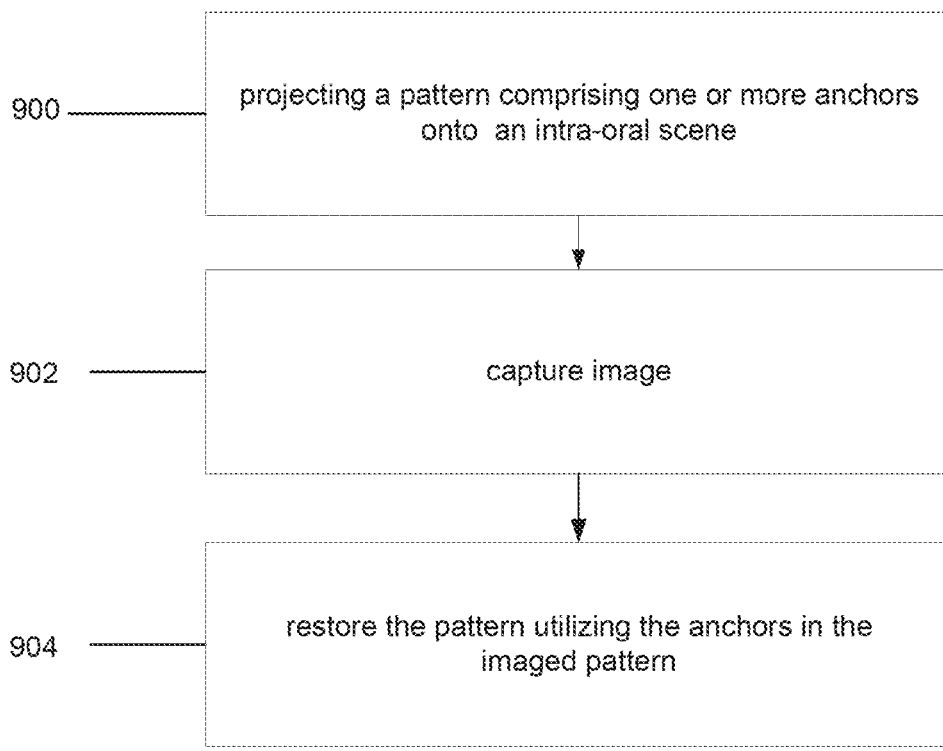
FIG. 9 is a flowchart of a method for scanning an intra-oral scene using a pattern comprising one or more anchors, according to some embodiments of the invention.

FIG. 9 is a flowchart of a method for scanning an intra-oral scene using a pattern comprising one or more anchors, according to some embodiments.

In some embodiments, a pattern comprising one or more anchors is projected onto an intra-oral scene (900). In some embodiments, anchoring is implemented by variations between the pattern entities, for example in a stripe based pattern anchors may be realized by one or more variations in stripe width, alignment, color, missing portions, and/or other variations suitable to provide unequivocal indexing of the anchor during restoring of the pattern. In some embodiments, two or more types of anchors (e.g. variations in stripe width and missing portions) are combined in a single pattern. In some embodiments, additional anchors such as circles and/or short lines are incorporated in the pattern.

In some embodiments, anchoring is implemented by single stripe color decoding or by batch processing of a sequence of stripes. Optionally, when color coding is used, global indexing by stripe counting and/or order restriction may be performed during processing to further reduce errors in pattern restoration.

In some embodiments, the image is captured (902) and is then processed to restore the pattern, utilizing the one or anchors that were incorporated in the pattern (904).

A potential advantage of using anchors may include simplifying restoring of the pattern. Optionally, counting votes gathered from the various anchors distributed in the pattern are statistically integrated in the stripe indexing process, potentially reducing counting errors. Counting errors may be caused, for example, by stripe loss due to the scene geometry, shadows in the scene, tooth defects and/or other factors affecting the stripe shape, continuousness and/or alignment; stripe reconstruction failure and/or false detection of stripes may be caused for example by the different materials in the scene (e.g. teeth and gingiva), specular reflections from fluids in the scene (e.g. blood, saliva) and natural and/or cast shadows in the scene.

Another potential advantage of using anchors may include reducing ambiguity, which may be caused as a result of one or more of: errors in pattern restoration, and/or depth discontinuities in the scene.

In some embodiments, the amount of anchors incorporated in the pattern is selected in accordance with the amount of smooth patches in the scene. A smooth patch may include a region with no or only a small amount of depth discontinuities.

Optionally, due to the relatively small amount of smooth patches in the intra-oral scene, a relatively small amount of anchors may be sufficient for restoring the pattern while maintaining stripe counting errors under a predefined threshold.

In some embodiments, the spread of anchors is selected taking into account the general structure of the imaged area as dictated by the optical characteristics of the image. For example, if an image of a full tooth takes up about ⅙ of field of view, at least one anchor should be present in each ⅙ portion (e.g square portion) of the projected pattern.

In some embodiments, a projected stripe is split into segments over the smooth patches. Optionally, this discontinuity is detected by algorithmic processing and taken into consideration during indexing, so as to reduce erroneous flowing of the indexing outside of a smooth patch.

In some embodiments, the amount, location and/or structure of anchors is selected to be sufficient for maintaining indexing errors under a predetermined threshold, for example under a threshold of 95%, 90%, 80% or intermediate, higher or lower detection percentages. The detection percentage may be defined as the percentage of pixels of the detected stripes that were indexed correctly.

In some embodiments, between 10-30 anchors, 5-10 anchors, 1-50 anchors or intermediate, larger or smaller amount of anchors are incorporated in a pattern.

In some embodiments, use of anchors having different signatures may provide for reducing ambiguity. Optionally, the amount of anchors having different signatures is selected to be small enough so as to facilitate restoration of the anchors. In some embodiments, in which a scene comprises only a few smooth patches, iterative region growing and confidence thresholding can be applied upon the pattern entities.

In some embodiments, anchors of various types and/or combinations of anchors are used. For example, a pair of anchors of a first type (e.g. missing portions in the stripes) is positioned near a pair of anchors of a second type (e.g. between 30 to 45 degrees and/or between 45 to 60 degrees and/or between 60 to 90 degrees). A potential advantage of pairing anchors of a certain type and/or combining anchors of various types may resolve anchor ambiguity and thereby improve detection and reducing of indexing errors.

Figure 10:
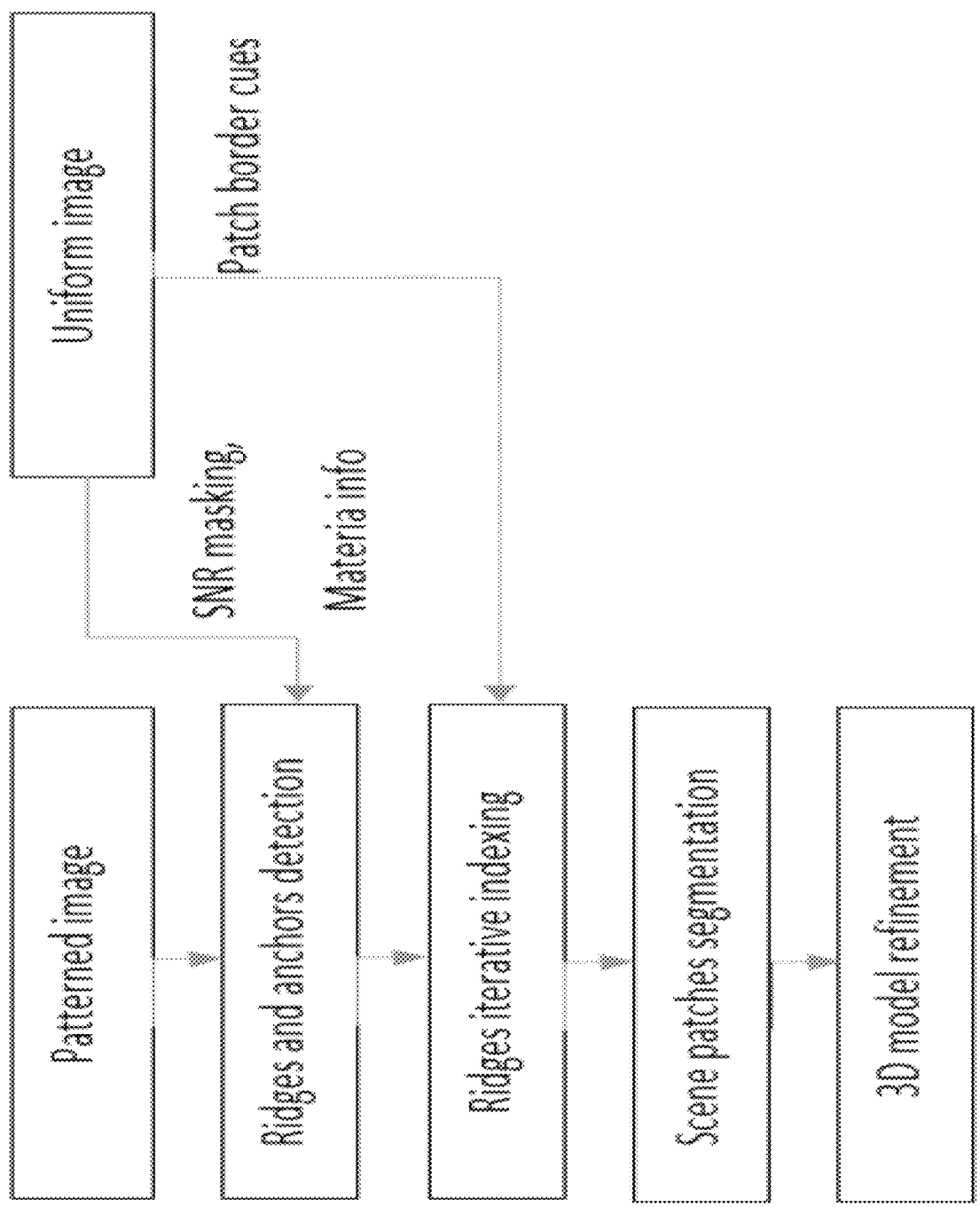
FIG. 10 is a flowchart of a method for processing an imaged pattern, according to some embodiments of the invention.

FIG. 10 is a flowchart of a method for processing an imaged pattern, according to some embodiments of the invention.

In some embodiments, processing of the patterned image comprises detecting ridges and/or anchors in the pattern. A "ridge" as referred to herein may include a central long axis of a stripe; additionally or alternatively, the implied ridge can be evaluated as the center of the separating stripe, i.e. the line connecting the points which are the farthest from the "light" ridges mentioned beforehand in parallel to the stripes color change direction.

In some embodiments, detection of the ridges and/or anchors is performed using information obtained from an image that was acquired under uniform lighting. Optionally, one or more boundaries in the scene are determined using the uniform light image. For example, depth discontinuities in the scene and/or other areas prone to projected stripe loss are detected using the uniform light image. Optionally, smooth patches or borders thereof are assessed using the uniform light image. In some embodiments, assessment of smooth patches and/or their boundaries is carried out using constant parameterized segmentation, adaptive segmentation, multi-color edge detection and/or other techniques.

In some embodiments, detection of patch boundaries splits the scene into a plurality of entities, thereby potentially reducing indexing "overflow" which may occur when different pattern entities such as stripes are erroneously detected as being connected to each other.

In some embodiments, once smooth patches are identified, detection and indexing of the stripes may be achieved according to the anchors of each smooth patch, under the assumption that the smooth patch does not comprise any missing stripes or parts of a stripe.

In some embodiments, in which the pattern comprises recurring entities such as stripes with dark regions between the stripes (e.g. in a referential pattern as described hereinabove), the dark regions may carry cues of stripe discontinuities. For example, if the darkest spot of a vertical line between two ridges of neighboring stripes is off-centered (i.e. is not equally distant from the two ridges), the deviation from the center may be correlative to a depth change in the scene. Additionally or alternatively, the center between two lines that follow some percentage of the maximum of the projected line, for example 10, 30, 50% or intermediate, larger or smaller value is used.

In some embodiments, ridges of the dark regions serve as pattern entities as well. Optionally, by integrating two spread functions of neighboring light stripes, the dark region ridge can be identified according to the lowest point of the function.

In some embodiments, the imaged sustainability of the dark regions to the variety of imaged materials is different from that of the light stripes. Optionally, integrating count of dark regions' ridges into the stripe indexing process may reduce the likelihood of indexing errors. In some embodiments, assessing a width of a dark region is performed to identify whether a light stripe or portion thereof is missing.

In some embodiments, iterative indexing of the ridges provides for segmenting the scene into smooth patches. In an example, a monotonic increment of the indexing along a column combined with connectivity of the ridges parallel to rows defines separate patches. In some embodiments, following the indexing process, each ridge is given a number based on its location with respect to one or more anchors. If no errors have occurred, the order of numbers given to the ridges (per each smooth patch) should be monotonic. If such order is not maintained, either an error has occurred and/or a smooth patch boundary was reached.

A potential advantage of dividing the imaged scene into independent patches may include increasing a degree of precision of the 3D model of the scene. In some embodiments, separation into patches may help maintain precision requirements during construction of the model at areas adjacent patch border lines, especially following processes such as outlier removal processes and/or resampling processes and/or smoothing processes.

In some embodiments, the detected patch boundaries are taken into account during refinement of the 3D model, for example so that smoothing of the model is performed without smoothing across the boundaries, (since they are indicative of a shifting depth in the scene).

Figure 11:
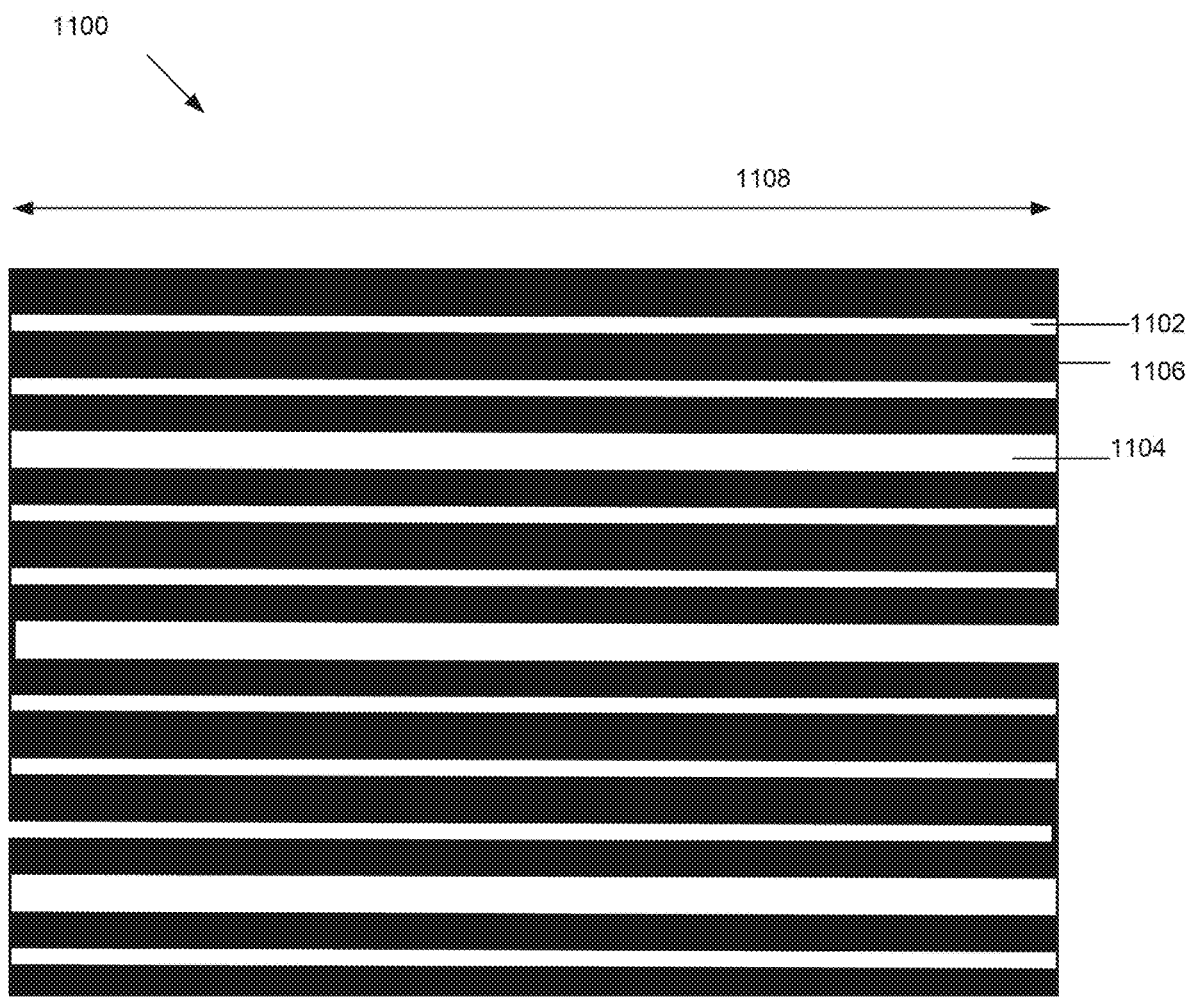
FIG. 11 is an example of a monochrome pattern comprising stripes having various widths, according to some embodiments of the invention.

FIG. 11 is an example of a monochrome pattern 1100 comprising stripes having various widths, according to some embodiments of the invention.

In some embodiments, the pattern comprises stripes having at least two different widths, 3 different widths, 5 different widths or intermediate, larger or smaller number. In some embodiments, a constant width factor is introduced. In the example shown herein, pattern 1100 comprises 3 entities: a stripe 1102 of a first width, a wider stripe 1104 and a dark region or spacing 1106. Optionally, indexed portions of, for example, the wide stripe 1104 and/or narrow stripe 1102 and/or combination thereof are used as anchors for stripe counting, in one or both directions along the baseline 1108 (i.e. the line extending between imager's optical aperture and the projecting light source), for columns that contain the indexed portion.

In some embodiments, a width of the black regions is selected so as to "compensate" for the varying widths of the stripes, for example so that the distances between stripe centers remain constant.

A potential of using a monochrome pattern for example as described herein may include simplifying projection, reducing power requirements and/or reducing the effective modulation transfer function of the imager. These may provide for an imager of a small form factor.

Figure 12:
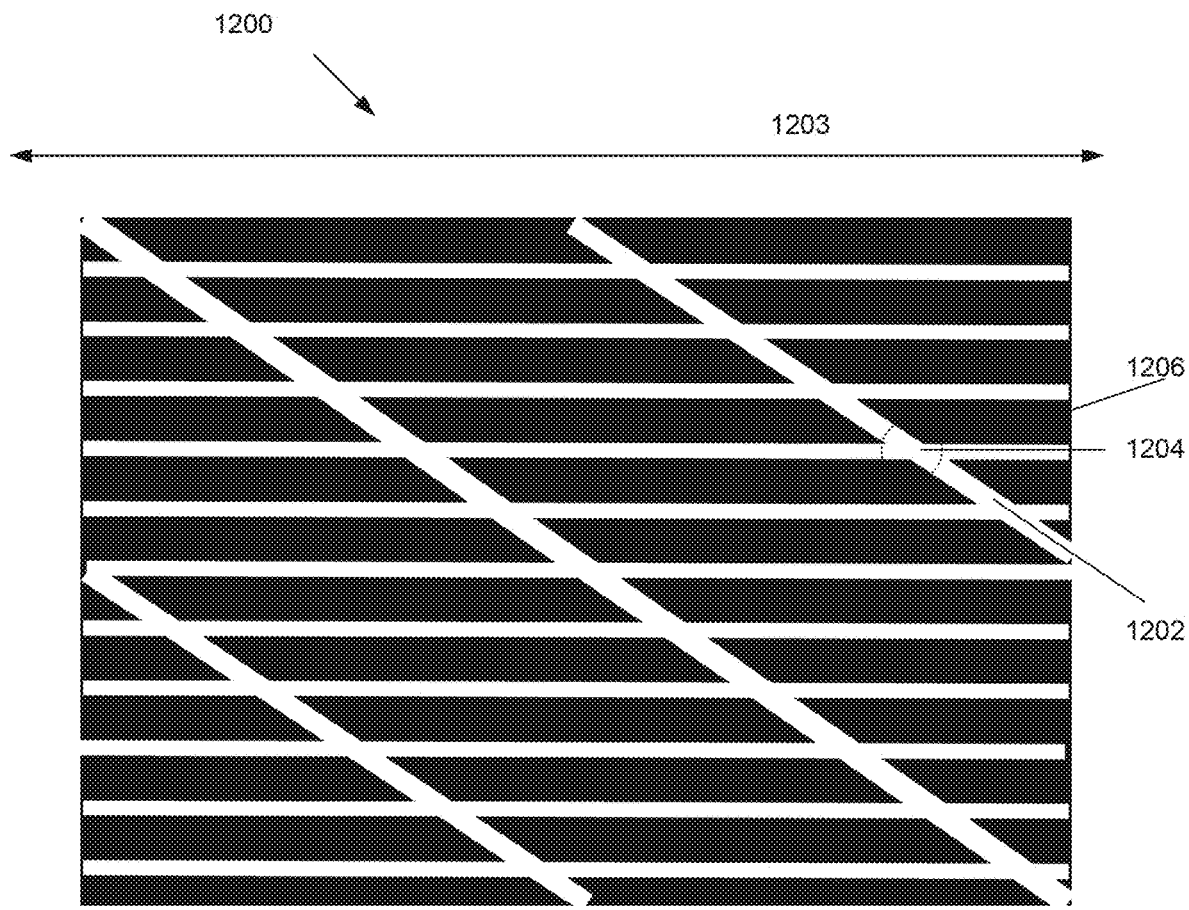
FIG. 12 is a an example of a monochrome pattern comprising one or more diagonals, according to some embodiments of the invention.

FIG. 12 is an example of a monochrome pattern 1200 comprising one or more diagonals, according to some embodiments of the invention.

In some embodiments, one or more diagonals 1202 are incorporated in the pattern. In some embodiments, diagonal 1202 crosses at least two stripes of the pattern, producing junctions 1204 with a crossed stripe. On each of the stripes, the junction is formed at a horizontal location which is different than junction location of the same diagonal with other stripes. In some embodiments, the horizontal location contributes to indexing of the stripes, since the horizontal location in a reflected stripe remains similar to the one that was projected. In some embodiments, detection of junctions in a certain sector of rows and columns in the acquired image can be traced to a specific diagonal and the stripe it crosses, thereby limiting the number of possibilities and resolving ambiguity between the different diagonals.

In some embodiments, the number of diagonals is selected according to possible vertical movement of the reflected stripes as the stripes are returned from various depths in the scene. Additionally or alternatively, the number of diagonals is selected to be sufficient to maintain indexing errors under a predefined threshold.

In some embodiments, an angle between the diagonal and the baseline is between 10-80 degrees, such as 30 degrees, 45 degrees, 50 degrees, 60 degrees or intermediate, larger or smaller angles. In some embodiments, the angle is selected in accordance with a distance between stripes and/or in accordance with stripe width, for example so that a horizontal distance between two adjacent junctions will be above a predefined threshold for accurately identifying the junctions.

In some embodiments, a geometrical position of the diagonals in the pattern is selected so that one or more diagonals would be located at a predefined region in the received image when the pattern is returned from a surface at a known distance, e.g. returned from approximately a middle of the depth of the focus range. In an example, a diagonal is positioned in the pattern so that it extends from an upper left corner of the image to the bottom right corner of the image.

In some embodiments, the diagonal lines are surrounded by dark area when they cross the horizontal stripe. The dark area can be similar in thickness to the dark area between the stripes or smaller or larger. A potential advantage of a dark area at the crossing may include facilitating detection of the diagonals.

In some embodiments, spacing between adjacent diagonals is selected to be sufficient to reduce a likelihood of the imaged diagonals intersecting each other.

In some embodiments, additional signatures are incorporated to facilitate detection and/or reduce ambiguities in diagonal detection.

FIGS. 13A-B are examples of patterns comprising multiple color zones, according to some embodiments of the invention.

In some embodiments, stripes of the pattern are divided into multiple color zones, such as 2, 3, 4, 6, 8, color zones or intermediate, larger or smaller number. Optionally, each color zone comprises one or more stripes. In the examples shown herein, the patterns comprise 3 grayscale color zones.

In some embodiments, multiple color zones are utilized in color patterns as well.

In some embodiments, for example as shown in FIG. 13B, two or more coding strategies may be combined in a single pattern. For example, multiple color zones are used in a pattern comprising diagonals. In such combination, multiple color zones may be efficient to reduce ambiguity between the various diagonals in the pattern.

In some embodiments, color is incorporated in various components of the pattern, such as within one or more stripes; within areas between white stripes; within diagonals, wide stripes, and/or other anchors; within junctions; and/or other pattern components or combinations thereof.

In an example, a wide stripe comprises colored stripes adjacent it. Optionally, stripes above and below the wide stripe are different in color. Optionally, different wide stripes are surrounded by stripes of different colors, to allow for differentiating between the wide stripes.

In some embodiments, a color sequence is selected to obtain a large distance in the color space between spatially close colors. The color space may include RGB, HSV, CMY, CMYK and/or other color spaces.

Figure 14:
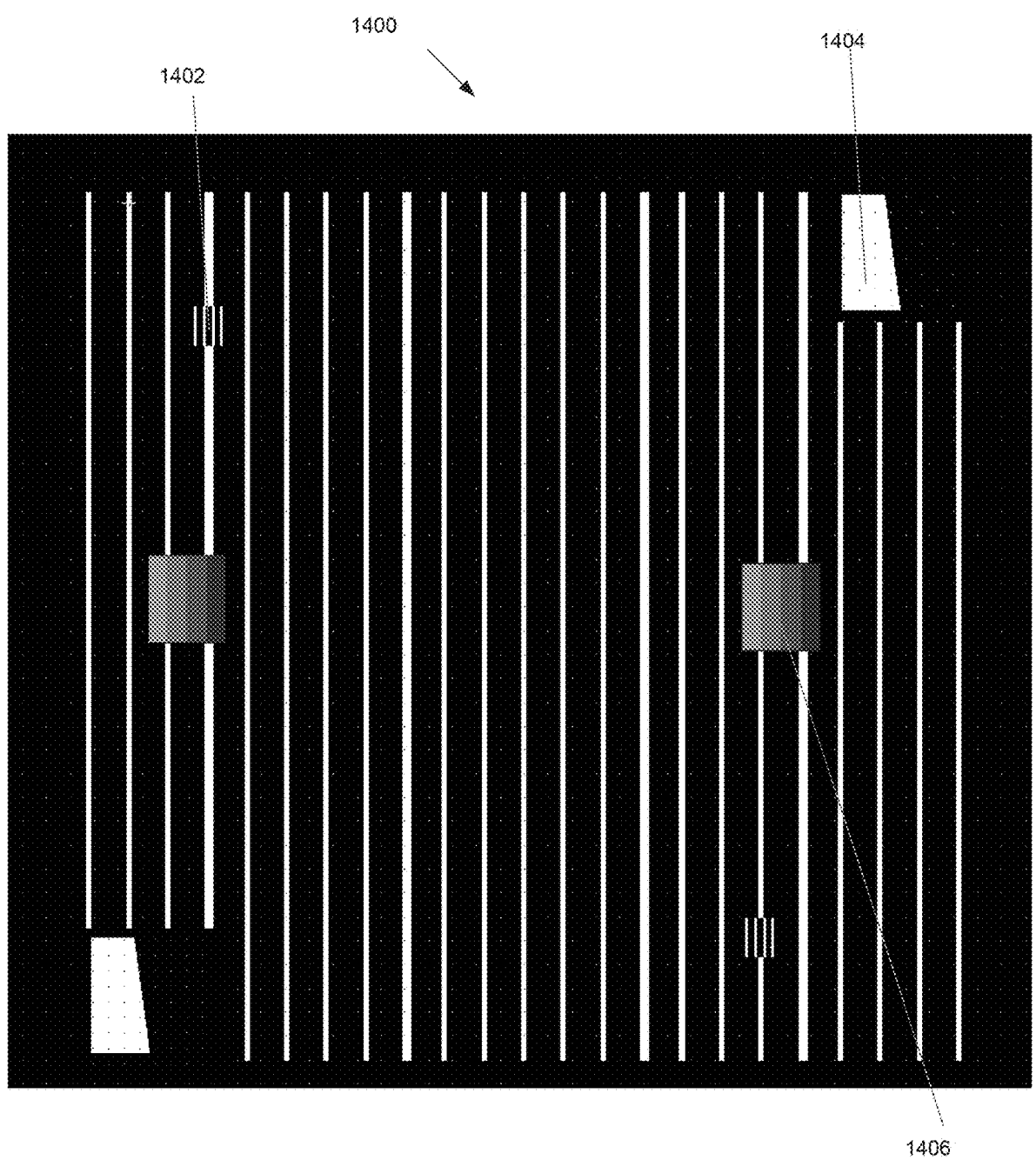
FIG. 14 is an example of a pattern comprising one or more calibration elements, according to some embodiments of the invention.

FIG. 14 is an example of a pattern 1400 comprising one or more calibration elements, according to some embodiments. In some embodiments, a calibration element comprises one or more shapes, colors, and/or other entities configured to facilitate quantifying the optical characteristics of the scene and/or of the optical characteristics of the scanner, such as focus and/or reflection direction and/or color. Exemplary calibration elements include one or more of: fine lines set at varying distances from each other 1402; a checkered board arrangement; a block having a slanted edge 1404, and/or other elements suitable to facilitate optical calibration, such as calibrate the MTF of the optical system for example using MTF measurements known in the art. Optionally, a calibration element comprises entities of different colors, for example grayscale entities as shown in element 1406, which can be used to calibrate, for instance, LED power or exposure.

In some embodiments, positioning of the calibration elements is selected so that at least one calibration element is visible in the imager's field of view as the depth changes and the imager captures different areas of the projected pattern. In some embodiments, the calibration elements are removed from the detected image using image processing techniques.

It is noted that scanning patterns incorporating combinations of coding schemes for example as described hereinabove are also contemplated by this application. For example, a color coded pattern may include stripes of various widths; a color coded pattern may include diagonals; a color coded pattern may include a probe window; a monochrome pattern may include stripes of various widths and diagonals; and/or other combinations.

In some embodiments, a referential pattern is used for accurate extraction of illuminated objects (e.g. tooth, inlays, crowns, gums, tongue, carry, gloves or other intraoral features) and/or geometry. Optionally, the referential pattern includes multiple projected entities. Optionally, at least some of the projected entities have a different spectral footprint.

In some embodiments, the following process is performed:
  Illuminate object with a referential pattern
  Take an image
    Optionally an image is made of the objects illuminated by the referential pattern
    Optionally one or more spectral images are made of the objects illuminated by the referential pattern and/or two or more spectral bands are differentiated Optionally take also an ambient image (e.g. without pattern illumination)

Optionally take also an image with uniform illumination

Optionally take also an image with uniform white illumination

Correct pattern features colors for example by

Optionally using non illuminated areas in said referential pattern.

Optionally differentiating projected entities based on their spectral footprint

Optionally using uniform illumination image and/or ambient image as described herein above.

Compute a depth map of the surface of one or more illuminated objects

Figure 15:
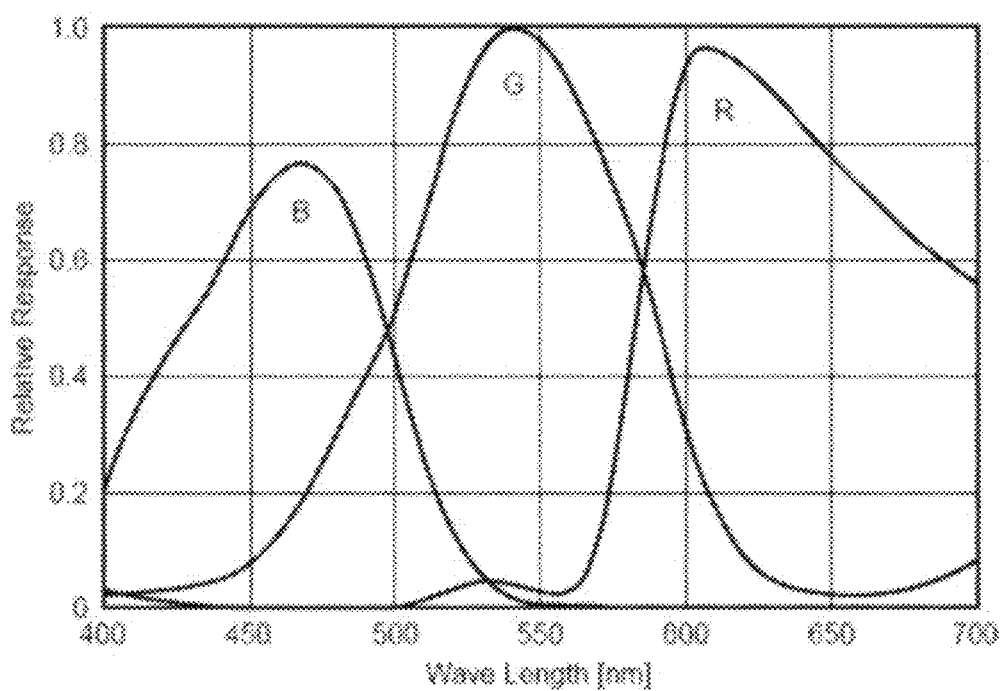
FIG. 15 is an exemplary illustration of color sensitivity bands of a Bayer filer (source U.S. Pat. No. 9,593,982 FIG. 2).

FIG. 15 is an exemplary illustration of color sensitivity bands of a Bayer filer (source U.S. Pat. No. 9,593,982 FIG. 2). In some cases the sensitivity bands of a Bayer filter may be wide. For example, the pass band may range between 25 to 50 nm. For example, the transition band may range between 40 to 100 nm. The sensitivity in the overlap between bands may be as high as 50% of the sensitivity in the pass band.

In some embodiments, a hyperspectral camera with bands such as schematically shown at FIG. 5B can include a set of narrowband filters within the range 400-500 nm and/or within the visible range 400-700 nm and/or visible and IR range 400-850 nm and/or another spectral range. In some embodiments, narrow color bands may have a passband width FWHM (Full Width Half Max) ranging between 80 to 15 nm and/or 40 to 10 nm and/or 20 to 5 nm and/or less than 5 nm. For example narrow color bands may have a transition band width ranging between 50 to 25 nm and/or from 25 to 15 nm and/or 15 to 10 nm and/or 10 to 5 nm and/or less than 5 nm. Optionally, a sensor array may be focused in long wavelength light for example ranging between 500 to 600 nm and/or between 600 to 700 nm.

In some embodiments, crosstalk may be reduced by selecting an order of bands. For example, the spectral signature of neighboring projected entities may be selected to have reduced spectral cross talk. For example, entity colors may be chosen to create large spatial distance between entities that are close in the frequency domain. For example a set stripes may be ordered with a center of their band range at staggered rather than in strictly increasing or decreasing order. For example, the order of range centers may be 550, 400, 600, 450, 650, 500, 700, 550. For example this gives a minimal 150 nm difference and even distribution. If the bands where ordered on strict increasing or decreasing would have a distance of 50 nm neighboring bands.

Figure 16:
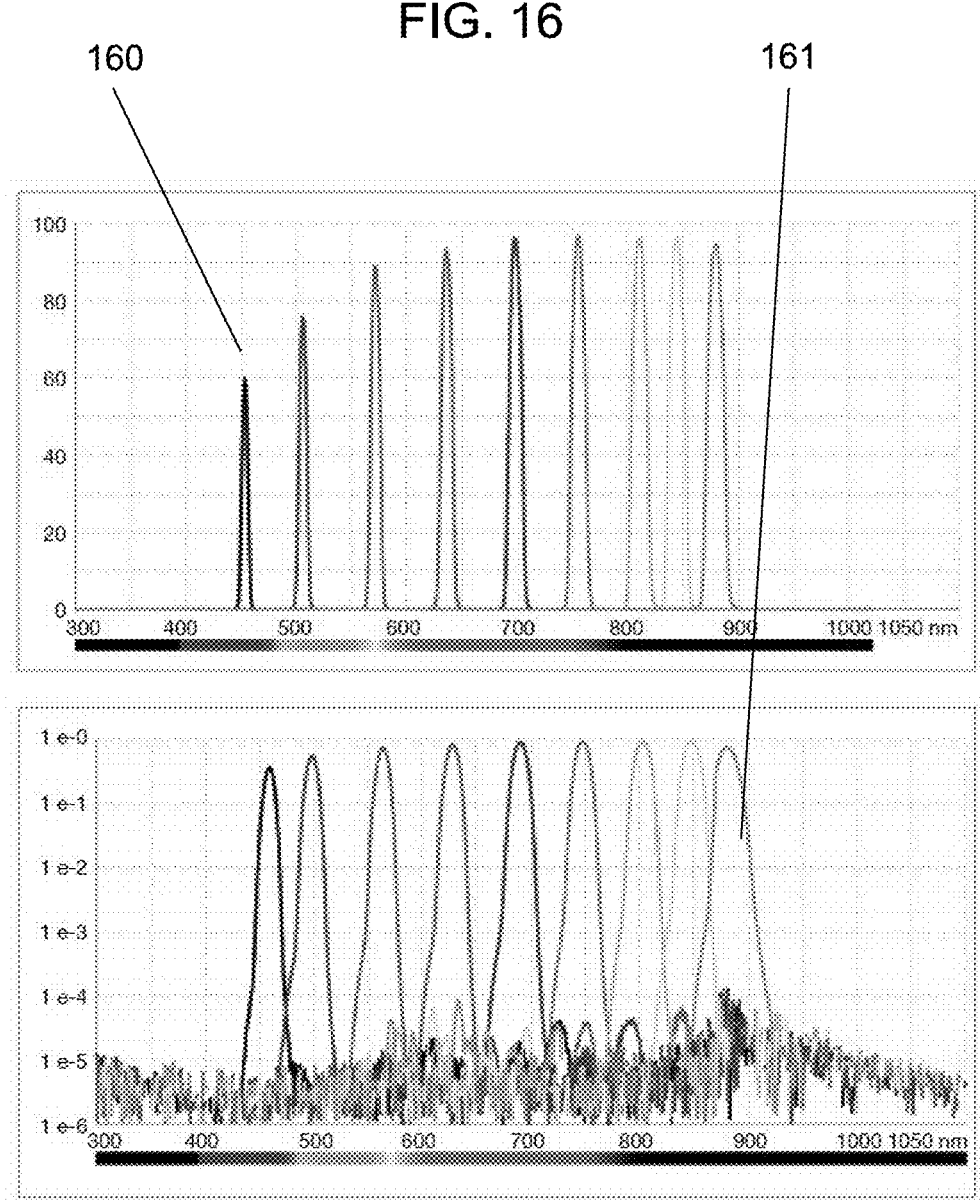
FIG. 16 illustrates additional options of narrowband filters with different levels of spectral crosstalk in accordance with embodiments of the current invention.

FIG. 16 illustrates additional options of narrowband filters with different levels of spectral crosstalk in accordance with an embodiment of the current invention. In some embodiments, decreasing the band width and/or the overlap between bands, for example as illustrated by bands 160, decreases the crosstalk between different bands. In some cases, decreasing the band width decreases also the transmitted light and the detection SNR. Increasing the band width, for example as illustrated by bands 161 may in some cases increase the detection SNR. Increasing the bandwidth may also increase spectral crosstalk and/or may reduce the chance of error in identification of the correct projected structure.

Figure 17:
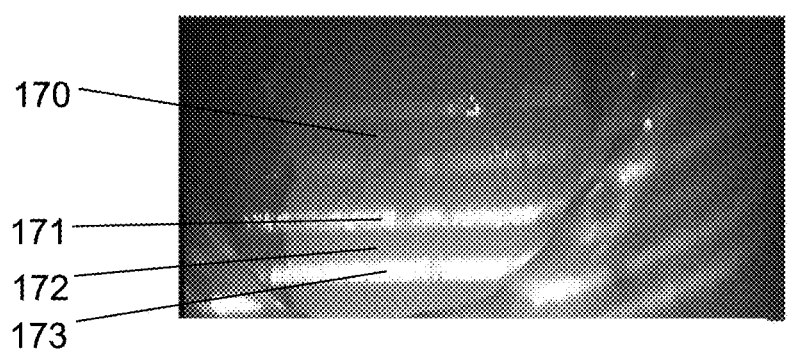
FIG. 17 illustrates an image of referential stripes pattern illuminated over a tooth in accordance with an embodiment of the present invention.

FIG. 17 illustrates an image of referential stripes pattern illuminated over a tooth in accordance with an embodiment of the present invention. For example, the image of FIG. 17 is monochromatic. Alternatively or additionally, spectral features, for example color images may be captured as well. For example, as described before, after obtaining the depth map of tooth 170, the image is corrected locally for the known PSF of the optical system (e.g. referential pattern projector and imager). Tooth 170 is optionally illuminated by stripes 171 (green) and 173 (blue) with a referential black gap 172 in-between. In FIG. 17, the effect of scattering can be seen in that black gap 172 is illuminated by light that migrate through tooth 170 from other stripes.

Ambient Estimation

In some embodiments, the ambient illumination is estimated by taking an image without any illumination (e.g. pattern or uniform illumination). Optionally, an image of a referential pattern may be corrected by subtracting the effect of the ambient light. For example, after subtracting the effect of ambient illumination, the corrected image may be used for identification of said referential pattern colors and/or for depth mapping.

In some embodiments stripe colors are estimated by dividing the image of the pattern illumination by image of uniform white illumination. In some embodiments stripe colors is estimated by dividing the image of pattern illumination after ambient subtraction by image of uniform white illumination. For example, the division may help reduce confounding effects on the depth mapping due to local variations in the color of tissue.

FIGS. 18A and 18B illustrate structures of a sensor array in accordance with embodiments of the current invention. In some embodiment a sensor array (for example a CMOS) will be used to capture an image. Alternatively or additionally, an image can be captured by scanning a scene. In some embodiment, use of a sensor array has an advantage of producing the image of multiple colors and/or multiple locations simultaneously. For example, the senor array may reduce problems due to movement and/or changes in lighting over time. For example, simultaneously producing a multi-color image may make it easier to relate between features seen different bands.

In some embodiments a sensor array will include spectral sensors (marked B1-B5 in FIG. 18A) and/or wide band sensors (for example a monochrome sensor sensitive to the entire visible spectrum (e.g. without a filter)) marked C in FIG. 18A. For example, there may be a large number of high sensitivity large band filters to capture the geometry of projected entities. Optionally, a smaller number of color filtered sensors are used for spectral differentiate of the projected entities. In some embodiments the colored pixels may be covered with narrowband filters, such as interference filters. The wideband sensors may have higher sensitivity since the color filter absorbs some of the light. Additionally or alternatively, the wideband sensors may sense all the projected colored features (e.g. all the lines in a colored lines pattern). For example, the wideband sensors may be used to provide higher accuracy in locating the feature in the image (e.g. locating a line in accuracy of 1/10 pixel). Optionally, higher accuracy 2D images are used to produce higher depth accuracy. In some embodiments, the pattern of sensors on a sensor array and/or the order of scanning of a scanning sensor may be adjusted to improve imaging of the pattern of the projected entities. For example, for a projected pattern of horizontal lines (for example as illustrated in FIG. 17) the sensors in a sensor array may be arranged perpendicular to the stripes (e.g. in vertical columns of similar sensors as illustrated in FIG. 18B). For example, this may give good resolution of the position of the lines in each spectral band and/or enable good depth accuracy. Alternatively or additionally, the lines of sensors in the array may be another angle (e.g. diagonal and or between 30 to 45 degrees and/or between 45 to 60 degrees and/or between 60 to 90 degrees) with respect to the lines on the pattern and may provide better sampling of the measured space while the 3D scanner is scanned over the object. Alternatively or additionally a column of sensors may include multiple colors.

In some embodiments, the mix of sensor may be adjusted according to the range of colors to be measured. For example, using the 3 colors of RGB Bayer filter over a CMOS, to detect a pattern that is focused in the violet-blue-green range the sensors mix may include an increased number of blue filters. For example for a blue pattern, the blue pixels may have improved sensitivity over green pixels and/or the red pixels may have the lower sensitivity then the green. Optionally the sensor array will include increased blue and green sensors (pixels) and decreased red pixels (for example the red pixels may be useful for imaging specular areas). For instance the Bayer pattern (CFA—Color Filter Array) can be G B B R instead of the common RGB which is B G G R. In some embodiments the contrast of the blue spectrum of the projected lines is better. For example an increased number of blue pixels in the filter array may provide better accuracy of locating the projected pattern (e.g. lines) and/or better depth accuracy.

The terms "comprises", "comprising", "includes", "including", "having" and their conjugates mean "including but not limited to".

The term "consisting of" means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular form "a", "an" and "the" include plural references unless the context clearly dictates otherwise. For example, the term "a compound" or "at least one compound" may include a plurality of compounds, including mixtures thereof.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

As used herein, the term "treating" includes abrogating, substantially inhibiting, slowing or reversing the progression of a condition, substantially ameliorating clinical or aesthetical symptoms of a condition or substantially preventing the appearance of clinical or aesthetical symptoms of a condition.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

What is claimed is:

1. A structured light scanning method for structured light scanning of an intra-oral scene, comprising:
    projecting onto an intra-oral scene a color-coded pattern comprising color entities separated from each other by dark regions;
    acquiring an image of the intra-oral scene; and
    determining one or more depths in said intra-oral scene based on:
        detecting said projected pattern in the acquired image of said scene;
        differentiating color entities in the acquired image using color filters; and
    subtracting color obtained in an adjacent dark region from color obtained in a color entity of interest, thereby reducing crosstalk.

2. The method of claim 1, wherein said intraoral scene comprises teeth.

3. The method of claim 1, wherein said subtracting comprises subtracting colored light of at least one projected colored entity which is scattered through a tooth and emerges back to said image at a spatial location of a different projected colored entity.

4. The method of claim 1, wherein said dark regions are sized to reduce crosstalk.

5. The method according to claim 1, wherein said acquiring is performed using a color imager having a Bayer filter.

6. The method according to claim 1, wherein said detecting comprises determining colors in the imaged pattern using said dark regions as reference.

7. The method according to claim 1, wherein said pattern comprises colored stripes separated from each other by dark regions in the form of stripes.

8. The method according to claim 1, wherein said determining one or more depths comprises indexing said color entities of said pattern, and wherein said dark regions define entities of the pattern which can be indexed in addition to said color entities.

9. The method of claim 1, further comprising restoring said projected pattern by associating an imaged entity to a projected entity by identifying the wavelength band of said projected entity in said image.

10. The method of claim 9, further comprising differentiating between said color entities by separating between at least two spectral bands wherein at least one of said spectral bands is a narrow band wherein said differentiating is performed using at least two narrowband filters.

11. The method claim 10, wherein at least one of said at least two narrowband filters captures at least 95% of the pixels of said at least one spectral band.

12. The method according to claim 1, further comprising:
constructing a 3D model of the scene using inner-image information obtained from said image acquired under unstructured lighting and inner-image information obtained from said image acquired under said patterned lighting; and
said constructing comprises identifying borders of smooth patches in the scene, wherein:
said borders indicative of depth discontinuities, and
said smooth patches are indexed in a continuous manner.

13. The method of claim 1 and further comprising:
imaging said projected pattern as a plurality of pixels in an acquired image of said scene using a hyperspectral imager positioned to image said scene, wherein said hyperspectral imager comprises interference filters attached to pixels of said hyperspectral imager;
estimating the color of each pixel for associating said pixel with said projected color-coded pattern; and
determining depth in said scene according to said associating.

14. The method of claim 4, wherein crosstalk is reduced by sizing said dark regions so as to avoid geometrical overlap between the imaged entities.

15. The method of claim 1, wherein said pattern comprises parallel stripes.

16. The method of claim 1, wherein said dark region comprises a non-illuminated area.

17. The method of claim 12, wherein said unstructured lighting comprises uniform lighting;
wherein information obtained from said image acquired under unstructured lighting is used for one or more of:
coloring of the reconstructed scene,
assessment of a geometry of the scene,
evaluation of reflection characteristics of contents of the scene, and
assessment of locations prone to loss of a projected pattern entities.

18. The method according to claim 5, wherein a sensor array of said Bayer filter includes increased numbers of blue pixels.

19. The method according to claim 1, wherein said pattern comprises one or more calibration element for quantifying, from said image, one or more optical characteristic of one or both of:
said intra-oral scene; and an imager performing said acquiring.

20. The method according to claim 1, wherein said differentiating comprises estimating a scattering factor of a local material and subtracting scattering according to said scattering factor.

21. The method according to claim 1, wherein said subtracting comprises subtracting a weighted averages of colors obtained in said adjacent dark region, where weighting of said averages is according to a distance from said color entity of interest.

22. The method according to claim 1, wherein said subtracting comprises subtracting ambient illumination.

* * * * *